United States Patent [19]

Bossert et al.

[11] 4,038,399
[45] July 26, 1977

[54] 1,4-DIHYDROPYRIDINE CARBOXYLIC ACID ESTERS USEFUL AS CORONARY VESSEL DILATORS AND ANTI-HYPERTENSIVES

[75] Inventors: Friedrich Bossert; Horst Meyer, both of Wuppertal; Wulf Vater, Opladen, all of Germany

[73] Assignee: Bayer Aktiengesellschaft, Germany

[21] Appl. No.: 647,414

[22] Filed: Jan. 8, 1976

Related U.S. Application Data

[62] Division of Ser. No. 548,395, Feb. 10, 1975, Pat. No. 3,974,275, which is a division of Ser. No. 350,381, April 12, 1973, Pat. No. 3,905,970.

[30] Foreign Application Priority Data

Apr. 18, 1972 Germany .............................. 2218644

[51] Int. Cl.$^2$ ........................................... A61K 31/455
[52] U.S. Cl. .................................................... 424/266
[58] Field of Search ................ 424/266; 260/295.5 R, 260/294.9, 295 AM

[56] References Cited

U.S. PATENT DOCUMENTS

| | | | |
|---|---|---|---|
| 3,488,359 | 1/1970 | Bossert et al. | 424/266 |
| 3,905,970 | 9/1975 | Bossert et al. | 424/266 |

*Primary Examiner*—Leonard Schenkman
*Attorney, Agent, or Firm*—Jacobs & Jacobs

[57] ABSTRACT

1,4-dinydropyridine carboxylic acid esters of the formula:

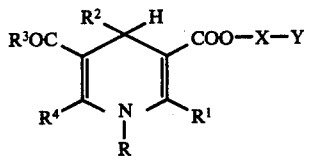

or a pharmaceutically acceptable nontoxic salt thereof wherein R, $R_1$, $R_2$, $R_3$, $R_4$, X and Y are defined hereinafter are useful for their coronary activity, particularly as coronary vessel dilators and as antihypertensives.

22 Claims, No Drawings

1,4-DIHYDROPYRIDINE CARBOXYLIC ACID ESTERS USEFUL AS CORONARY VESSEL DILATORS AND ANTI-HYPERTENSIVES

This is a division of Ser. No. 548,395 filed Feb. 10, 1975, now U.S. Pat. No. 3,974,275 which is a divisional of Ser. No. 350,381, filed Apr. 12, 1973, which issued as U.S. Pat. No. 3,905,970 on Sept. 16, 1975.

The present invention is concerned with 1,4-dihydropyridine carboxylic acid esters, processes for their production, pharmaceutical compositions in which said compound is the active agent, and their medicinal use in humans and animals as coronary active agents, particularly for their coronary vessel dilating effect and their antihypertensive effective.

It has already been disclosed that 1,4-dihydropyridines possess interesting pharmacological properties (F. Bossert and W. Vater, "Die Naturwissenschaften" 1971, 58th year, Issue 11, page 578).

The present invention comprises 1,4-dihydropyridine carboxylic acid esters of the formula:

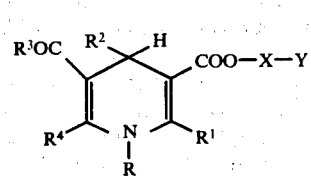

(I)

or pharmaceutically acceptable, nontoxic salts thereof wherein

R is hydrogen, straight- or branched-chain lower alkyl, lower alkenyl or lower alkynyl;

$R^1$ and $R^4$ are the same or different and are each hydrogen or straight- or branched-chain lower alkyl;

X is straight- or branched-chain lower alkylene;

Y is α-, β- or γ-pyridyl, or the moiety NR'R" wherein R' and R" are the same or different and are each hydrogen or lower alkyl, or R' and R", together with the nitrogen atom to which they are attached, form a 5-, 6- or 7-membered heterocyclic ring wherein said nitrogen atom is the only heteroatom, or a 5-, 6- or 7-membered heterocyclic ring which has at least one additional heteroatom selected from the group consisting of oxygen, sulphur, NH or N-(lower alkyl);

$R^2$ is aryl unsubstituted or substituted by 1, 2 or 3 substituents selected from the group consisting of nitro, cyano, azido, lower alkyl, lower alkoxy, lower acyloxy, carb-(lower alkoxy), amino, lower acylamino, lower alkylamino, di-(lower alkylamino), $SO_n$-(lower alkyl) wherein n is 0, 1 or 2, phenyl, trifluoromethyl and halogen; benzyl; phenylethyl; styryl; cycloalkyl; cycloalkenyl; or napthyl, quinolyl, isoquinolyl, pyridyl, pyrimidyl, pyrryl, furyl or thenyl unsubstituted or substituted by one or more substituents selected from the group consisting of lower alkyl, lower alkoxy, nitro and halogen; and $R^3$ is a straight- or branched-chain lower hydrocarbon unsubstituted or substituted by one or two hydroxyl groups, a straight- or branched-chain lower hydrocarbon interrupted by one or two oxygen atoms, the moiety —OQ wherein Q is straight, branched or cyclic, saturated, partially unsaturated or unsaturated lower hydrocarbon unsubstituted or substituted by one or two hydroxyl groups, a straight, branched or cyclic, saturated, partially unsaturated or unsaturated lower hydrocarbon interrupted by one or two oxygen atoms or the moiety O—X'—Y' wherein X' is straight- or branched-chain lower alkylene and Y' is α-, β- or γ-pyridyl, or the moiety NR'R" wherein R' and R" are the same or different and are each hydrogen or lower alkyl or R' and R" together with the nitrogen atom to which they are attached from a 5-, 6- or 7-membered heterocyclic ring wherein said nitrogen atom is the only heteroatom or a 5-, 6- or 7-membered heterocyclic ring which has at least one additional heteroatom selected from the group consisting of oxygen, sulphur, NH or N-(lower alkyl).

In addition to their coronary vessel dilating effect and antihypertensive effect, the compounds of the present invention are also useful for their antifibrillation action, vascular spasmolytic action, muscular spasmolytic action and for their action on the cholesterol lever and lipid level of the blood.

According to one embodiment of the present invention

R is hydrogen, straight- or branched-chain alkyl of 1 to 4 carbon atoms or straight- or branched-chain alkenyl of 2 to 4 carbon atoms;

$R^1$ and $R^4$ are the same or different and are each hydrogen or straight- or branched-chain alkyl of 1 to 4 carbon atoms;

X is straight- or branched-chain alkylene of 1 to 4 carbon atoms;

Y is α-, β- or γ-pyridyl, or the moiety NR'R" wherein R' and R" are the same or different and are each hydrogen or alkyl of 1 to 4 carbon atoms, or R' and R" together with the nitrogen atom to which they are attached from a 5-, 6-, or 7-membered heterocyclic ring wherein said nitrogen atom is the only heteroatom, or a 5-, 6- or 7-membered heterocyclic ring which has at least one additional heteroatom selected from the group consisting of oxygen, sulphur, NH or N-(lower alkyl);

$R^2$ is phenyl unsubstituted or substituted by 1 or 2 nitro, cyano, azido, alkyl of 1 to 4 carbon atoms, acetoxy, amino, acetylamino, alkylamino of 1 to 4 carbon atoms, dialkylamino of 1 to 4 carbon atoms in each alkyl moiety, chloro, bromo, or trifluoromethyl groups, or by a carb-(lower alkoxy) group or a moiety of the formula $SO_n$-alkyl wherein n is 0 or 2 and the alkyl moiety has 1 to 4 carbon atoms, or by 1 to 3 alkoxy groups of 1 to 4 carbon atoms; benzyl; phenylethyl; styryl; cycloalkyl of 5 or 6 carbon atoms; cycloalkenyl of 5 or 6 carbon atoms; or napthyl, quinolyl, isoquinolyl, pyridyl, pyrimidyl, pyrryl, furyl or thenyl unsubstituted or substituted by alkyl of 1 to 4 carbon atoms, alkoxy of 1 to 4 carbon atoms, nitro, chloro, bromo; and $R^3$ is the moiety —OQ wherein Q is straight- or branched-chain alkyl of 1 to 4 carbon atoms, or alkoxyalkyl of up to 6 carbon atoms in both moieties, or the moiety —O—X'—Y' wherein X' is straight- or branched-chain alkylene of 1 to 4 carbon atoms, and Y' is α-, β- or γ-pyridyl, or the moiety NR'R" wherein R' and R" are the same or different and are each hydrogen or alkyl of 1 to 4 carbon atoms, or R' and R" together with the nitrogen atom to which they are attached form a 5-, 6- or 7-membered heterocyclic ring wherein said nitrogen atom is the only heteroatom, or a 5-, 6- or 7-membered heterocyclic ring which has at least one additional heteroatom selected from the group consisting of oxygen, sulphur, NH or N-(lower alkyl).

It is preferred that the alkyl moiety of R has 1 to 3 carbon atoms and of $R^1$ and $R^4$ has one or two carbon atoms.

According to another embodiment of the present invention $R^2$ is phenyl unsubstituted or substituted by azido or $SO_n$-alkyl wherein $n$ is 0 or 2 and alkyl is of 1 to 4 carbon atoms, or by 1 or 2 amino moieties, alkylamino moieties of 1 or 2 carbon atoms, 1 or 2 acetylamino moieties, 1 or 2 acetoxy moieties, 1 or 2 alkyl moieties of 1 or 2 carbon atoms, 1 to 3 alkoxy moieties of 1 or 2 carbon atoms or 1 or 2 members selected from the group consisting of nitro, cyano, chloro, bromo and trifluoromethyl; benzyl; styryl; cycloakyl of 5 or 6 carbon atoms; cycloalkenyl of 5 or 6 carbon atoms; or naphthyl, quinolyl, isoquinolyl, pyridyl, pyrimidyl, pyrryl, furyl or thenyl unsubstituted or substituted by alkyl of 1 or 2 carbon atoms, alkoxy of 1 or 2 carbon atoms, nitro, chloro or bromo; and $R^3$ is the moiety —OQ wherein Q is straight- or branched-chain alkyl of 1 to 4 carbon atoms interrupted by 1 oxygen atom or the moiety —O—X'—Y' wherein X' is straight- or branched-chain alkylene of 1 to 4 carbon atoms, and Y' is α-, β- or γ-pyridyl, or the moiety NR'R" wherein R' and R" are the same or different and are each hydrogen or alkyl of 1 to 4 carbon atoms, or R' R" and together with the nitrogen atom to which they are attached form a 5-, 6- or 7-membered heterocyclic ring wherein said nitrogen atom is the only heteroatom, or a 5-, 6- or 7-membered heterocyclic ring which has at least one additional heteroatom selected from the group consisting of oxygen, sulphur, NH or N-(lower alkyl).

According to another embodiment of the present invention

R is hydrogen or straight- or branched-chain alkyl of 1 to 4 carbon atoms, $R^1$ and $R^4$ are the same or different and are each straight- or branched-chain alkyl of 1 to 4 carbon atoms, X is straight- or branched-chain alkylene of 1 to 4 carbon atoms, Y is α-, β- or γ-pyridyl, dimethylamino, diethylamino, morpholine, thiomorpholine, pyrrolidine or methylpiperazine.

$R^2$ is phenyl; phenyl substituted by 1 or 2 substituents selected from the group consisting of nitro, cyano, azido, carbethoxy, acetylamino, dimethylamino, $SO_n$-alkyl wherein $n$ is 0, 1 or 2 and the alkyl moiety has 1 or 2 carbon atoms, chloro and trifluoromethyl, or by 1 to 3 methoxy groups; styryl; napthyl; quinolyl; pyridyl; nitropyridyl; pyrimidyl; dimethoxypryrimidyl; furyl; bromofuryl; thenyl; or nitrothenyl; and $R^3$ is the moiety —OQ wherein Q is straight- or branched-chain alkyl of 1 to 4 carbon atoms, methoxyethyl or the moiety —O—X'—Y' wherein X' is straight- or branched-chain alkylene of 1 to 4 carbon atoms, and Y' is α-, β- or γ-pyridyl, morpholine, methylpyrrolidine or methylpiperazine.

According to another embodiment of the present invention

R is hydrogen or straight- or branched-chain alkyl of 1 to b 4 carbon atoms, $R^1$ is straight- or branched-chain alkyl of 1 to 3 carbon atoms, $R^4$ is straight- or branched-chain alkyl of 1 to 4 carbon atoms, X is straight- or branched-chain alkylene of 1 to 3 carbon atoms, Y is α-, β- or γ-pyridyl, diemthylamino, diethylamino, pyrrolidine, morpholine, thiomorpholine, or methylpiperazine, $R^2$ is phenyl; phenyl substituted by nitro, nitro and thiomethyl, nitro and trifluoromethyl, nitro and chloro, dinitro, trifluoromethyl, di-trifluoromethyl, chloro, dichloro, cyano, mercapto, methylsulphinyl, ethylsulphonyl, azido, dimethylamino, methoxy, methoxy and fluoro, trimethoxy, fluoro, carbethoxy or acetamino; styryl; napthyl; pyridyl; nitropyridyl; pyrimidyl; diemthoxypyrimidyl; brompfuryl; nitrothenyl; or quinolyl; and $R^3$ is straight- or branched-chain alkoxy of 1 to 4 carbon atoms, methoxyethoxy, pyridylmethoxy, morpholinoethoxy, morpholinoisopropoxy, propoxymethyliperazine, or ethylpyrrolidine.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pententyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

The term lower alkoxy denotes a straight or branched hydrocarbon chain bound to the remainder of the molecule through an ethereal oxygen atom as, for example, methoxy, ethoxy, propoxy, isopropoxy, butoxy, isobutoxy, pentoxy and hexoxy.

The term halogen denotes the substituents fluoro, chloro, bromo and iodo.

As indicated, the present invention also pertains to the pharmaceutically acceptable nontoxic salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitric acid, salicylic acid, phthalic acid, embonic acid, enanthic acid, and the like.

The compounds of the present invention may be produced by the following processes:

a. an acyl-fatty acid ester of the formula:

$$R^1-CO-CH_2-COO-X-Y- \quad (II)$$

is reacted with ammonia or with an amine of the formula:

$$H_2N-R \quad (III)$$

or a salt thereof, to produce an enamine of the formula:

$$\begin{array}{c} NH-R \\ | \\ R^1-C=CH-COO-X-Y \end{array} \quad (IV)$$

which is then reacted with or without intermediate isolation, with a ylidene derivative of the formula:

$$\begin{array}{c} O \\ \| \\ R^2-CH=C-C-R^4 \\ | \\ CO-R^3 \end{array} \quad (V)$$

to produce the desired compound; or b. a β-dicarbonyl compound of the formula:

$$R^4-CO-CH_2-CO-R^3 \quad (VI)$$

is reacted with ammonia or an amine of the formula:

$$H_2N-R \quad (III)$$

or a salt thereof, to produce an enamine of the formula:

$$\begin{array}{c} NH-R \\ | \\ R^4-C=CH-CO-R^3 \end{array} \quad (VII)$$

which is then reacted with or without intermediate isolation wih a ylidene derivative of the formula:

$$\begin{array}{c} R^2-CH=C-CO-R^1 \\ | \\ COO-X-Y \end{array} \quad (VIII)$$

to produce the desired compound; or c. a β-dicarbonyl compound of the formula:

$$R^4-CO-CH_2-CO-R^3 \quad (VI)$$

and an enamine of the formula:

$$\begin{array}{c} NH-R \\ | \\ R^1-C=CH-COO-X-Y \end{array} \quad (IV)$$

are reacted with an aldehyde of the formula:

$$R^2-CHO \quad (IX)$$

to produce the desired compound; or d. an acyl-fatty acid ester of the formula:

$$R^1-CO-CH_2-COO-X-Y \quad (II)$$

and an enamine of the formula:

$$\begin{array}{c} NH-R \\ | \\ R^4-C=CH-CO-R^3 \end{array} \quad (VII)$$

are reacted with an aldehyde of the formula:

$$R^2-CHO \quad (IX)$$

to produce the desired compound; or e. two moles of an acyl-fatty acid ester of the formula:

$$R^1-CO-CH_2-COO-X-Y \quad (II)$$

and one mole of ammonia or an amine of the formula:

$$H_2N-R \quad (III)$$

or a salt thereof, are reacted with an aldehyde of the formula:

$$R^2-CHO \quad (IX)$$

to produce the desired compound; or f. a 1,4-dihydropyridine derivative of the formula:

$$\begin{array}{c} R^3OC \quad R^2 \quad H \quad COOZ \\ \diagup \quad \diagdown \\ R^4 \quad N \quad R^1 \\ | \\ R \end{array} \quad (X)$$

wherein
z is hydrogen or an alkali meta or alkaline earth metal cation
is reacted with a compound of the formula $$Hal-X-Y \quad (XI)$$

wherein Hal is chlorine or bromine to produce the desired compound.

In the above formulae II to XI, R, $R^1$, $R^2$, $R^3$, $R^4$, X and Y are all as defined above.

Throughout this specification the different reactions (a) to (f) will be referred to respectively as Process Variants (a) to (f).

In Process Variants (a), (b) and (e), the amine of formula III will be ammonia when a compound in which R is a hydrogen atom is being prepared.

Surprisingly, the compounds of the present invention exhibit, for the same strength of effect, a considerably better solubility than known 1,4-dihydropyridines.

If 3'-nitrobenzylideneacetoacetic acid methyl ester, acetoacetic acid (α-pyridyl)-methyl ester and methylamine are used as starting materials, with N-methylaminocrotonic acid (α-pyridyl)-methyl ester as the intermediate enamine, which need not be isolated, the course of the reaction for Process Variant (a) can be represented as follows:

Scheme 1

-continued

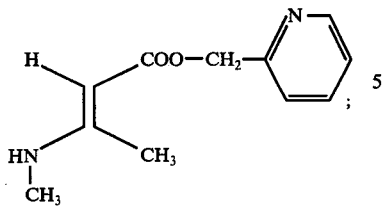

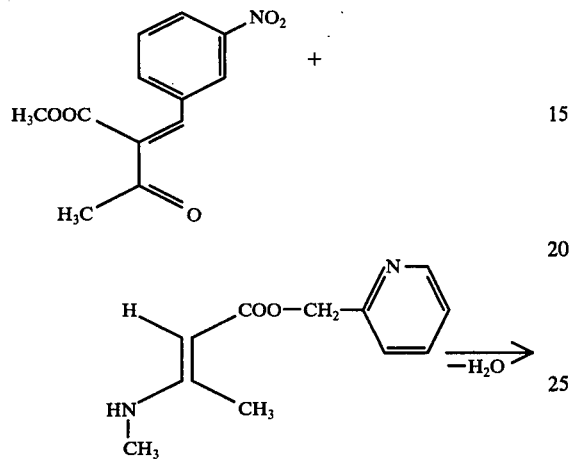

If 3'-nitrobenzylideneacetoacetic acid (α-pyridyl)-methyl ester, acetoacetic acid methol ester and methylamine are used as the starting materials, with N-methylaminocrotonic acid methyl ester as the optionally isolated intermediate enamine, the course of the reaction for Process Variant (b) is as follows:

Scheme 2

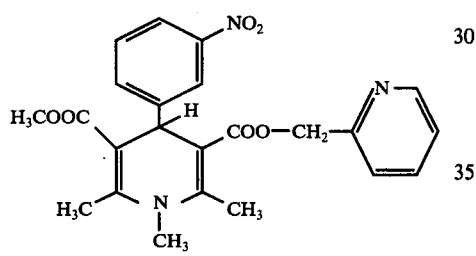

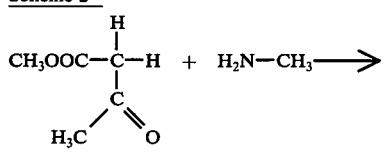

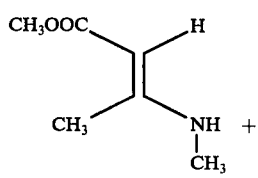

-continued

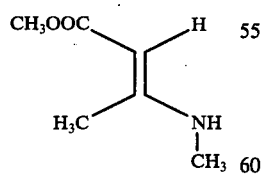

If 2-nitrobenzaldehyde, acetoacetic acid methyl ester and aminocrotonic acid (β-pyridyl)-methyl ester are used as starting materials, the course of the reaction of Process Variant (c) takes place according to the following equation:

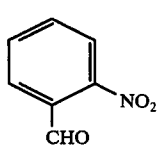

If 2-nitrobenzaldehyde, aminocrotonic acid methyl ester and acetoacetic acid (β-pyridyl)-methyl ester are used as starting materials, the course of the reaction for Process Variant (d) can be represented as follows:

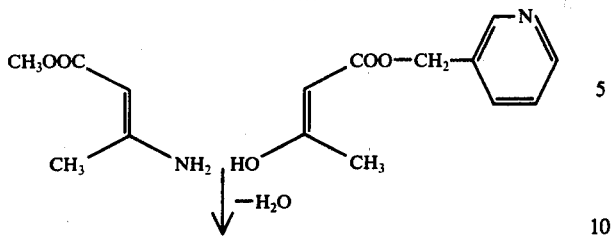
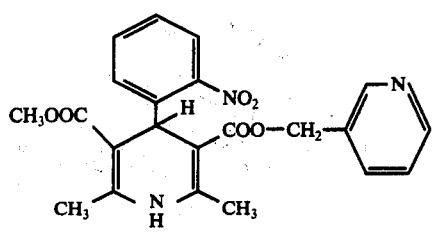

If 2-trifluoromethylbenzaldehyde, acetoacetic acid (β-N-morpholine)-ethyl ester and ammonia are used as starting materials, aminocrotonic acid (β-N-morpholine)-ethyl ester being the intermediate enamine, the course of the reaction for Process Variant (e) is as follows:

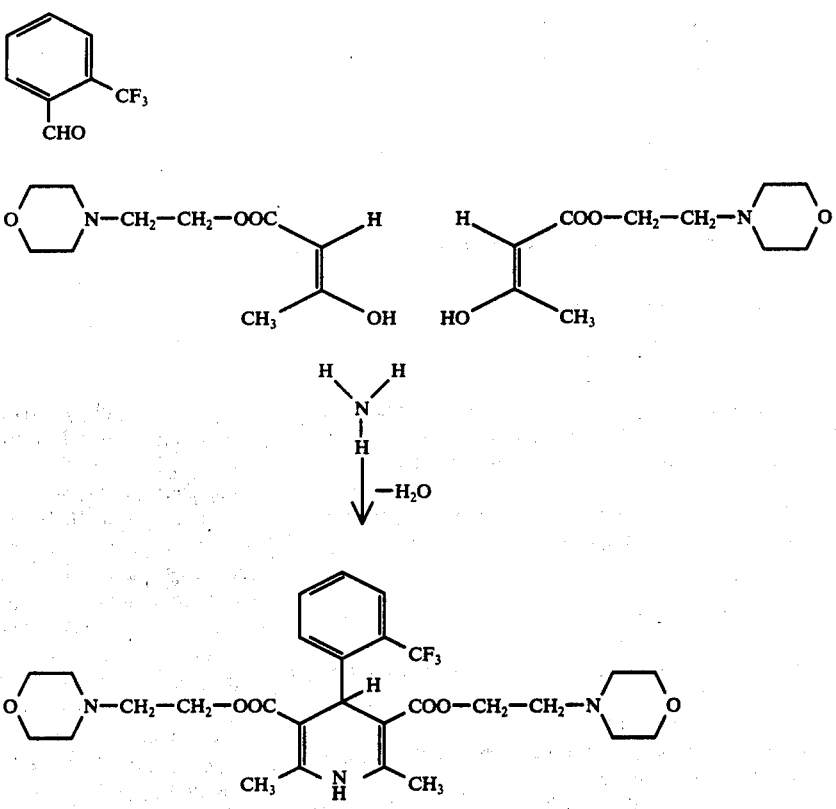

If a 1,4-dihydropyridine-monocarboxylic acid is used as starting material, the reaction for Process Variant (f) is as follows:

1) 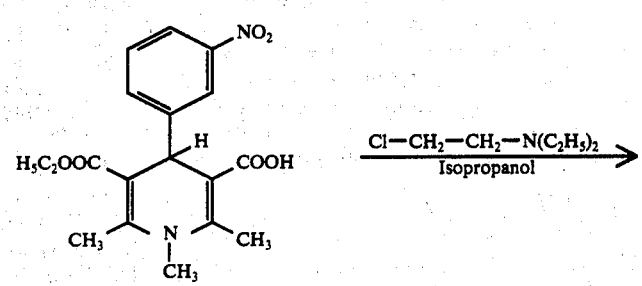

-continued

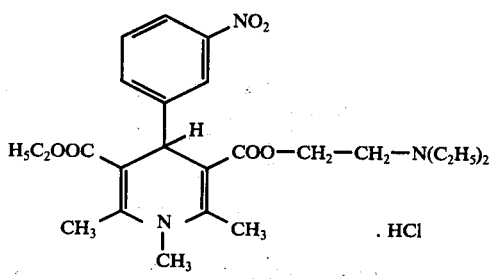

2)

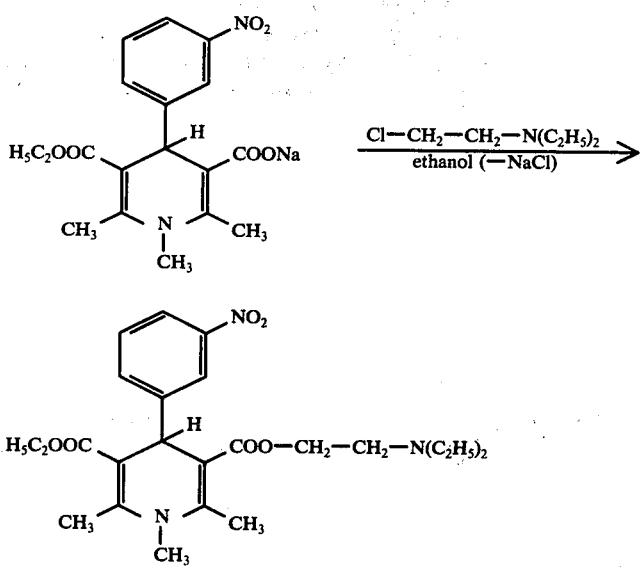

The 1,4-dihydropyridine-monocarboxylic acids used as starting materials in Process Variant (f) can be prepared by alkaline saponification of the 1,4-dihydropyridine-3,5-dicarboxylic acid diesters.

A. In the compounds of the invention and in the basically-substituted β-ketocarboxylic acid esters of the formula:

$$R^1-CO-CH_2COO-X-Y \qquad (II)$$

$R^1$ is preferably hydrogen or straight- or branched-chain alkyl of 1 to 4 carbon atoms, especially alkyl of 1 to 2 carbon atoms;

X is preferably straight- or branched-chain alkylene of 1 to 4 carbon atoms; and Y is preferably α-, β- or γ-pyridyl or NR'R" wherein R' and R" are each hydrogen or straight- or branched-chain alkyl of 1 to 4 carbon atoms, or R' and R", together with the nitrogen atom to which they are attached form a 5-, 6- or 7-membered heterocyclic ring wherein said nitrogen is the only heteroatom or the ring contains oxygen, sulfur NH or N-(lower alkyl) as an additional ring member.

The basic-substituted β-ketocarboxylic acid esters of the formula II used as starting materials in Process Variants (a) and (d) according to the invention were not previously known but can be produced according to known processes, for example, from diketene and basic-substituted alcohols (Chemical Abstracts 50, 16668 h (1956)).

As examples of these esters there may be mentioned:
Basic-substituted β-ketocarboxylic acid esters
Acetoacetic acid (α-pyridyl) -methyl ester,
acetoacetic acid (β-pyridyl)-methyl ester,
acetoacetic acid (γ-pyridyl)-methyl ester,
acetoacetic acid (β-N-morpholine)-ethyl ester,
acetoacetic acid (N-morpholine)-isopropyl ester,
acetoacetic acid (β-N-piperidine)-ethyl ester,
acetoacetic acid (β-N-piperidine)-isopropyl ester,
acetoacetic acid (β-N-thiomorpholine)-ethyl ester,
acetoacetic acid (β-N-thiomorpholine)-isopropyl ester,
acetoacetic acid (β-N-pyrrolidine)-ethyl ester,
acetoacetic acid (β-N,N'-methylpiperazine)-ethyl ester,
propionylacetic acid (α-pyridyl)-methyl ester,
propionylacetic acid (β-N-morpholine)-ethyl ester,
butyrylacetic acid (β-pyridyl)-methyl ester,
isobutyrylacetic acid (γ-pyridyl)-methyl ester,
acetoacetic acid (β-diethylamino)-ethyl ester and
acetoacetic acid (γ-dimethylamino)-propyl ester.

In the compounds of the invention, and in the amines of the formula:

$$H_2N-R \qquad (III)$$

used as starting materials in Process Variants (a), (b) and (e), R is preferably hydrogen or straight- or branched-chain alkyl of 1 to 4 carbon atoms or alkenyl of 2 to 4 carbon atoms, especially alkyl of 1 to 3 carbon atoms.

The amines of formula III used according to the invention are already known.

As examples of these amines there may be mentioned:
Amines:
Ammonia,
methylamine,
propylamine,
isopropylamine,
butylamine,
isobutylamine and allylamine.

In the enaminocarboxylic acid esters of the formula:

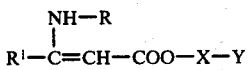
(IV)

R, R¹, X and Y are preferably as above defined for formulae II and III.

The enaminocarboxylic esters used as intermediates in Process Variants (a) and (c) according to the invention are not previously known but can be produced according to known methods (A. C. Cope, J.A.C.S. 67, 1017 (1945)) from appropriate basic-substituted β-ketocarboxylic acid esters.

As examples of these enaminocarboxylic acid esters there may be mentioned:

Basically-substituted enaminocarboxylic acid esters
β-Aminocrotonic acid (β-N-morpholine)-ethyl ester,
β-aminocrotonic acid (γ-pyridyl)-methyl ester,
β-N-methyl-aminocrotonic acid (α-pyridyl)-methyl ester,
β-N-ethylaminocrotonic acid (N,N'-methylpiperazine)-isopropyl ester and
β-N-allylaminocrotonic acid (N-thiomorpholine)-propyl ester.

In the compounds according to the invention, and in the ylidene derivatives of the formula:

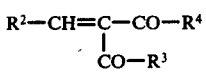
(V)

which are used as starting materials in Process Variant (a):

R² is preferably phenyl unsubstituted or substituted by 1 or 2 nitro groups, especially by one nitro group, by one cyano group, by one azido group, by 1 or 2 trifluoromethyl groups, especially by one trifluoromethyl group, by one SO$_n$-alkyl group wherein $n$ is 0 or 2 and the alkyl moiety has 1 to 4 carbon atoms, by 1 or 2 alkyl groups, by 1 to 3 alkoxy groups, by 1 or 2 acetoxy, amino, acetylamino, alkylamino or dialkylamino groups, each alkyl or alkoxy moiety having 1 to 4, especially 1 or 2, carbon atoms, or by 1 or 2 chlorine or bromine atoms, with the total number of the substituents being at most 3; or R² is benzyl, styryl, cycloalkyl of 5 or 6 carbon atoms or cycloalkenyl of 5 or 6 carbon atoms; or R² is pyridyl, pyrimidyl, naphthyl, quinolyl, isoquinolyl, thenyl, pyrryl or furyl unsubstituted or substituted by alkyl or alkoxy of 1 to 4 carbon atoms, especially of 1 or 2 carbon atoms, by nitro or by halogen, especially chlorine or bromine, R³ is preferably a straight- or branched-chain hydrocarbon of 1 to 4 carbon atoms unsubstituted or substituted by hydroxyl or interrupted by oxygen; or R³ is the moiety —OQ wherein Q is a straight, branched or cyclic, saturated, partially unsaturated or unsaturated hydrocarbon of 1 to 6 carbon atoms unsubstituted or substituted by hydroxyl or by oxygen; or R³ is the moiety —O—X'—Y' wherein X' is straight- or branched-chain alkylene or 1 to 4 carbon atoms, and Y' is α-, β- or γ-pyridyl, or the moiety NR'R" wherein R' and R" are the same or different and are each hydrogen or alkyl of 1 to 4 carbon atoms, or R' and R" together with the nitrogen atom to which they are attached form a 5-, 6- or 7-membered heterocyclic ring wherein said nitrogen atom is the only heteroatom, or a 5-, 6- or 7-membered hererocyclic ring which has at least one additional heteroatom selected from the group consisting of oxygen, sulphur, NH or N-(lower alkyl); and R⁴ is preferably hydrogen or straight- or branched-chain alkyl of 1 to 4 carbon atoms, especially of 1 to 2 carbon atoms.

The ylidene-β-ketocarboxylic acid esters of the formula V which are used according to the invention are already known or can be produced according to known methods (Org. Reactions, XV, 204 FF, (1967)).

As examples, there may be mentioned:
Ylidene-β-ketocarboxylic acid esters:
Benzylideneacetoacetic acid methyl ester,
2'-nitrobenzylideneacetoacetic acid methyl ester,
2'-nitrobenzylideneacetylacetone,
benzylideneacetylacetone,
3'-nitrobenzylideneacetoacetic acid methyl ester,
3'-nitrobenzylideneacetoacetic acid propargyl ester,
3'-nitrobenzylideneacetoacetic acid allyl ester,
3'-nitrobenzylideneacetoacetic acid β-methyoxyethyl ester,
3'-nitrobenzylideneacetoacetic acid β-ethoxyethyl ester,
3'-nitrobenzylideneacetoacetic acid isopropyl ester,
3'-nitrobenzylideneacetylacetone,
4'-nitrobenzylideneacetylacetone,
4'-nitrobenzylideneacetoacetic acid β-propoxyethyl ester,
4'-nitrobenzylideneacetoacetic acid n-propyl ester,
3'-nitro-6'-chlorobenzylideneacetoacetic acid methyl ester,
2'-cyanobenzylideneacetoacetic acid methyl ester,
2'-cyanobenzylideneacetoacetic acid ethyl ester,
2'-cyanobenzylidenepropionylacetic acid ethyl ester,
3'-cyanobenzylidenenacetoacetic acid methyl ester,
3'-nitro-4'-chlorobenzylideneacetylacetone,
3'-nitro-4'-chlorobenzylideneacetoacetic acid t-butyl ester,
3'-nitro-4'-chlorobenzylideneacetoacetic acid methyl ester,
2'-nitro-4-methoxybenzylideneacetoacetic acid methyl ester,
2'-cyano-4'-methylbenzylideneacetoacetic acid ethyl ester,
2'-azidobenzylideneacetoacetic acid ethyl ester,
3'-azidobenzylideneacetylacetone,
2'-methylmercaptobenzylideneacetoacetic acid methyl ester,
"-methylmercaptobenzylideneacetoacetic acid isopropyl ester,
2'-sulphinylmethylbenzyideneacetoacetic acid ethyl ester,
2'-sulphonylmethylacetoacetic acid allyl ester,
4-sulphonylmethylacetoacetic acid ethyl ester,
(1'-naphthylidene)-acetoacetic acid methyl ester,
(1'-naphthylidene)-acetoacetic acid ethyl ester,
(2'-naphthylidene)-acetoacetic acid ethyl ester,
(2'-ethoxy-1'-naphthylidene)-acetoacetic acid methyl ester,
(2'-methoxy-1'-naphthylidene)-acetoacetic acid ethyl ester, 5'-bromo-(1'-naphthylidene)-acetoacetic acid methyl ester,
(2'-quinolyl)-methylideneacetoacetic acid ethyl ester,
(3'-quinolyl)-methylideneacetoacetic acid methyl ester,
(4'-quinolyl)-methylideneacetoacetic acid ethyl ester,
(8'-quinolyl)-methyl-ideneacetoacetic acid ethyl ester,
(1'-isoquinolyl)-methylideneacetoacetic acid methyl ester,
(3'-isoquinolyl)-methylideneacetoacetic acid methyl ester,
α-pyridylmethylideneacetoacetic acid methyl ester,
α-pyridylmethylideneacetoacetic acid ethyl ester,
α-pyridylmethylideneacetoacetic acid allyl ester,
α-pyridylmethylideneacetoacetic acid cyclohexyl ester,
β-pyridylmethylideneacetoacetic acid β-methoxyethyl ester,
γ-pyridylmethylideneacetoacetic acid methyl ester,
6-methyl-α-pyridylmethylideneacetoacetic acid ethyl ester,
4',6'-dimethoxy-(5'-pyrimidyl)-methylideneacetoacetic acid ethyl ester,
(2'-thenyl)-methylideneacetoacetic acid ethyl ester,
(2'-furyl)-methylideneacetoacetic acid allyl ester,
(2'-pyrryl)-methylideneacetoacetic acid methyl ester,
3'-nitro-benzylidenepropionylacetic acid ethyl ester,
α-pyridylmethylidenepropionylacetic acid methyl ester,
α-pyridylmethylideneacetylacetone,
2'-, 3'- and 4'-methoxybenzylideneacetoacetic acid ethyl ester,
2'-, 3'- and 4'-methoxybenzylideneacetylacetone,
2'-methoxybenzylideneacetoacetic acid allyl ester,
2'-methoxybenzylideneacetoacetic acid propargyl ester,
2'-methoxybenzylidene-β-methoxyethyl ester,
2'-isopropoxybenzylideneacetoacetic acid ethyl ester,
3'-butoxybenzylideneacetoacetic acid methyl ester,
3',4',5'-trimethoxybenzylideneacetoacetic acid allyl ester,
2'-methylbenzylidenepropionylacetic acid methyl ester,
b 2'-, 3'- and 4'-methylbenzylideneacetoacetic acid ethyl ester,
2'-methylbenzylideneacetoacetic acid β-methoxyethyl ester,
2'-methylbenzylideneacetoacetic acid β-propoxyethyl ester,
2'-methylbenzylideneacetylacetone,
3',4'-dimethoxy-5'-bromobenzylideneacetoacetic acid ethyl ester,
2'-, 3'- and 4'-chloro/bromo/fluorobenzylideneacetoacetic acid ethyl ester,
2'-fluorobenzylideneacetoacetic acid ethyl ester,
3'-chlorobenzylideneacetylacetone,
3'-chlorobenzylidenepropionylacetic ethyl ester,
3'-chlorobenzylideneacetoacetic acid ethyl ester,
2'-chlorobenzylideneacetoacetic acid allyl ester,
2'-, 3'- and 4'-trifluoromethylbenzylidenacetoacetic acid propyl esters,
2'-trifluoromethylbenzylideneacetoacetic acid isopropyl ester,
3'-trifluoromethylbenzylideneacetoacetic acid methyl ester,
2'-carboethoxybenzylideneacetoacetic acid ethyl ester,
3'-carboxymethylbenzylideneacetoacetic acid methyl ester,
4-carboxyisopropylbenzylideneacetoacetic acid isopropyl ester, and
4'-carboxymethylbenzylideneacetoacetic acid allyl ester.

B. In the β-dicarbonyl compounds of the formula:

$$R^4-CO-CH_2-CO-R^3 \tag{VI}$$

used as starting materials in Process Variants (b) and (c), $R^3$ and $R^4$ preferably have the preferred meanings set forth above with respect to formula V.

The β-dicarbonyl compounds of the formula VI employed according to the invention are already known or can be produced by known processes (Pohl, Schmidt, U.S. Pat. No. 2,351,366 (1940), ref. in C.A. 1944, 5224).

Apart from the compounds already listed above, the following may be mentioned as examples:

β-Dicarbonyl Compounds:
Formylacetic acid ethyl ester,
acetoacetic acid methyl ester,
acetoacetic acid ethyl ester,
acetoacetic acid propyl ester,
acetoacetic acid isopropyl ester,
acetoacetic acid butyl ester,
acetoacetic acid (α- and β-)-methoxyethyl esters,
acetoacetic acid (α- and β-)-propoxyethyl esters,
acetoacetic acid (α- and β-)-hydroxyethyl esters,
acetoacetic acid allyl ester,
acetoacetic acid propargyl ester,
propionylacetic acid ethyl ester,
butyrylacetic acid methyl ester,
isobutyrylacetic acid ethyl ester,
acetoacetic acid furfuryl ester,
acetone-acid tetrahydrofurfuryl ester,
2,4-pentadione,
3,5-heptadione,
4,6-nonanedione, and
2,6-dimethyl-3,5-heptadione.

In the β-enaminocarbonyl compounds, used as starting materials in Process Variants (b) and (d), of the formula:

$$\begin{array}{c} NH-R \\ | \\ R^4-C=CH-CO-R^3 \end{array} \tag{VII}$$

$R$, $R^3$ and $R^4$ are preferably as above defined for formulae IV and V.

The β-enamino-carbonyl compounds of the formula VII employed according to the invention are already known or can be produced by known processes (A. C. Cope, J.A.C.S. 67, 1017 (1945)).

As examples there may be mentioned:
Enamino-keto compounds
β-Aminocrotonic acid methyl ester,
β-aminocrotonic acid ethyl ester,
β-aminocrotonic acid isopropyl ester,
β-aminocrotonic acid ethyl ester,
β-aminocrotonic acid β-methoxyethyl ester,
β-aminocrotonic acid cyclohexyl ester,
β-N-methylaminocrotonic acid methyl ester,
β-N-methylaminocrotonic acid ethyl ester,
β-N-methylaminocrotonic acid isopropyl ester,
β-N-ethylaminocrotonic acid ethyl ester,
β-N-isopropylaminocrotonic acid methyl ester,
β-N-methylaminocrotonic acid β-methoxyethyl ester,
1-amino-buten-1-en-3-one,
2-amino-penten-2-en-4-one and
2-methylamino-penten-2-en-4-one.

In the ylidene-β-keto compounds used according to the invention as starting materials in Process Variant (b), of the formula:

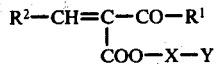 (VIII)

R¹, R², X and Y preferably are as above defined for formulae II and V.

The ylidene derivative of the formula VIII employed according to the invention are either known or can be produced by known methods (Org. Reactions XV, 204 ff, (1967)).

Apart from the compounds already listed above, the following may be mentioned as examples:
Ylidene-β-keto compounds
Benzylidene-acetoacetic acid (α-pyridyl)-methyl ester,
2'-nitrobenzylideneacetoacetic acid (β-N-morpholine)-ethyl ester,
2-trifluoromethylbenzylidene-acetoacetic acid (γ-N,N-methylpiperazine)-propyl ester,
2'-cyanobenzylideneacetoacetic acid (β-diethylamino)-ethyl ester,
α-pyridylmethylidenepropionylacetic acid (β-pyridyl)-methyl ester,
3'-chlorobenzylideneacetoacetic acid (β-N-thiomorpholine)-ethyl ester,
2'-sulphonylmethylbenzylideneacetoacetic acid (γ-pyridyl)-methyl ester,
(1'-naphthylidene)-acetoacetic acid (α-pyridyl)-methyl ester and
(8'-quinolylmethylideneacetoacetic acid (α-pyridyl)-methyl ester.

C. The aldehydes of the formula (IX) which can be used according to the invention as starting materials in Process Variant IX are already known or can be produced according to known methods (E. Mosettig, Org. Reactions, VIII, 281 ff. (1954)).

As examples there may be mentioned:
Aldehydes
Benzaldehyde,
2-, 3- and 4-methoxybenzaldehydes,
2-isopropoxybenzaldehyde,
3-butoxybenzaldehyde,
3,4-dihydroxymethylenebenzaldehyde,
3,4,5-trimethoxybenzaldehyde,
2-, 3- and 4-chloro/bromo/fluorobenzaldehyde,
2,4- and 2,6-dichlorobenzaldehyde,
2,4-dimethylbenzaldehyde,
3,5-diisopropyl-4-methoxybenzaldehyde,
2-, 3- and 4-nitrobenzaldehyde,
2,4- and 2,6-dinitrobenzaldehyde,
2-nitro-6-bromobenzaldehyde,
2-nitro-3-methoxy-6-chlorobenzaldehyde,
2-nitro-4-chlorobenzaldehyde,
2-nitro-4-methoxybenzaldehyde,
2-, 3- and 4-trifluoromethylbenzaldehyde,
2-, 3- and 4-dimethylaminobenzaldehyde,
4-dibutylaminobenzaldehyde,
4-acetaminobenzaldehyde,
2-, 3- and 4-cyanobenzaldehyde,
2-nitro-4-cyanobenzaldehyde,
3-chloro-4-cyanobenzaldehyde,
2-, 3- and 4-methylmercaptobenzaldehyde,
2-methylmercapto-5-nitrobenzaldehyde,
2-butylmercaptobenzaldehyde,
2-, 3- and 4-methylsulphinylbenzaldehyde,
2-, 3- and 4-methylsulphonylbenzaldehyde,
benzaldehyde-2-carboxylic acid ethyl ester,
benzaldehyde-3-carboxylic acid isopropyl ester,
benzaldehyde-4-carboxylic acid butyl ester,
3-nitrobenzaldehyde-4-carboxylic acid ethyl ester,
cinnamaldehyde,
hydrocinnamaldehyde,
formylcyclohexane,
1-formylcyclohex-3-ene,
1-formylcyclohex-1,3-ine,
1-formylcyclopent-3-ene,
α, β- and γ-pyridinaldehydes,
6-methylpyridine-2-aldehyde,
furan-2-aldehyde,
thiophen-2-aldehyde,
pyrrol-2-aldehyde,
2-, 3- and 4-azidobenzaldehydes,
pyrimidin-4-aldehyde,
5-nitro-6-methylpyridin-2-aldehyde,
1- and 2-naphthaldehyde,
5-bromo-1-naphthaldehyde,
quinolin-2-aldehyde,
7-methoxy-quinolin-4-aldehyde and
isoquinolin-1-aldehyde.

The 1,4-dihydropyridinemonocarboxylic acid employed as starting materials in Process Variant (f) according to the invention, of the formula:

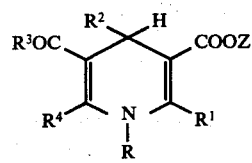

wherein R, R¹, R², R³, R⁴ and Z preferably have the preferred meanings set forth above, are as yet unknown and can be produced by alkaline hydrolysis of 1,4-dihydropyridine-3,5-dicarboxylic acid diesters.

As examples there may be mentioned:
1,4-Dihydropyridine-monocarboxylic acids
2,6-Dimethyl-4-(2'-nitrophenyl)-1,4-dihydropyridine-3-carboxylic acid-5-carboxylic acid ethyl ester,
2,6-dimethyl-4-(3'-trifluoromethylphenyl)-1,4-dihydropyridine-3-carboxylic acid methyl ester,
2,6-dimethyl-4-(3'-chlorophenyl)-dihydropyridine-3-carboxylic acid-5-carboxylic acid isopropyl ester,
1,2,6-trimethyl-4-(2'-nitrophenyl)-1,4-dihydropyridine-3-carboxylic acid-5-carboxylic acid methyl ester.
1,2,6-trimethyl-4-(3'-nitrophenyl)-1,4-dihydropyridine-3-carboxylic acid-5-carboxylic acid-5-carboxylic acid furfuryl ester,
1,2,6-trimethyl-4-(2'-chlorophenyl)-1,4-dihydropyridine-3-carboxylic acid-5-carboxylic acid propargyl ester,
1-methyl-2,6-diethyl-4-(2'-trifluoromethylphenyl)-1,4-dihydropyridine-3-carboxylic acid-5-carboxylic acid ethyl ester,
1,2,6-trimethyl-4-(1'-naphthyl)-1,4-dihydropyridine-3-carboxylic acid-5-carboxylic acid methyl ester,
1,2,6-triethyl-4-(4'-methylmercaptophenyl)-1,4-dihydropyridine-3-carboxylic acid-5-carboxylic acid butyl ester,
1,2,6-trimethyl-4-(α-pyridyl)-1,4-dihydropyridine-3-carboxylic acid-5-carboxylic acid methyl ester and 1,2,6-trimethyl-4-(4'-quinolyl)-1,4-dihydropyridine-3-carboxylic acid-5-carboxylic acid ethyl ester.

In all the Process Variants, water or any inert organic solvent can be used as diluent. Preferred diluents are alcohols (such as ethanol, methanol, and isopropanol), ethers (such as dioxane and diethyl ether), glacial acetic acid, dimethylformamide, dimethylsulphoxide, acetonitrile and pyridine.

The reaction temperatures can be varied over a substantial range. In general, the reaction is carried out at between 20° C and 150° C, preferably at the boiling point of the solvent.

The reactions can be carried out under normal pressure, but also at elevated pressure. In general, they are carried out under normal pressure.

In carrying out the processes according to the present invention, the substances participating in the reaction are generally employed approximately in molar amounts except where stated, and except for the amine or its salt which when used is appropriately added in an excess of 1 or 2 mols.

The following may be mentioned as representative important compounds according to the present invention:

2,6-Dimethyl-4-(2'-nitrophenyl)-1,4-dihydropyridine-3,5-dicarboxylic acid 3-(γ-dimethylamino)-propyl ester 5-methyl ester.

2,6-Dimethyl-4-(2'-methylsulphinylphenyl)-1,4-dihydropyridine-3,5-dicarboxylic acid 3-(N,N'-methyl-piperazino)-ethyl ester 5-butyl ester.

2,6-Diethyl-4-(2'-trifluoromethylphenyl)-1,4-dihydropyridine-3,5-dicarboxylic acid 3-(α-pyridyl)-methyl ester 5-methyl ester.

2-Methyl-6-ethyl-4-(3'-chlorophenyl)-1,4-dihydropyridine-3,5-dicarboxylic acid 3-(γ-N-morpholino)-propyl ester 5-isopropyl ester.

2,6-Isopropyl-4-(3'-nitrophenyl)-1,4-dihydropyridine-3,5-dicarboxylic acid 3-(β-pyridyl)-methyl ester 5-ethyl ester.

1,2,6-Trimethyl-4-(2'-4'-dinitrophenyl)-1,4-dihydropyridine-3,5-dicarboxylic acid 3-(γ-pyridyl)-methyl ester 5-methyl ester.

1-Methyl-2,6-diethyl-4-(2'-4'-ditrifluoromethylphenyl)-1,4-dihydropyridine-3,5-dicarboxylic acid di-(β-pyridyl)-methyl ester.

1,2,6-Triethyl-4-(3'-nitro-6'-chlorophenyl)-1,4-dihydropyridine-3,5-dicarboxylic acid 3-(β-thiomorpholino)-ethyl ester 5-ethyl ester.

1-Isopropyl-2,6-diethyl-4-(3'-fluorophenyl)-1,4-dihydropyridine-3,5-dicarboxylic acid di-(β-N-pyrrolidino)-ethyl ester.

1-Butyl-2,6-dimethyl-4-(3'-4'-5'-trimethoxyphenyl)-1,4-dihydropyridine-3,5-dicarboxylic acid 3-[2'-(2'-(α-pyridyl)-ethyl ester] 5-ethyl ester.

2,6-Dimethyl-4-(2'-cyanophenyl)-1,4-dihydropyridine-3,5-dicarboxylic acid 3-(γ-N,N'-methyl-piperazino)-propyl ester 5-methyl ester.

2,6-Diethyl-4-(4'-carbethoxyphenyl)-1,4-dihydropyridine-3,5-dicarboxylic acid 3-(α-pyridyl)-methyl ester 1,5-tert.-butyl ester.

2,6-Dimethyl-4-(5'-nitro-α-pyridyl)-1,4-dihydropyridine-3,5-dicarboxylic acid 3-(α-pyridyl)-methyl ester 5-ethyl ester.

2,6-Diethyl-4-(4'-trifluoromethylphenyl)-1,4-dihydropyridine-3,5-dicarboxylic acid 3-(β-N-morpholino)-ethyl ester 5-ethyl ester.

The compounds of the present invention are readily water-soluble in the form of salts (formed from acids) and do not require any solubilizing agent.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilating of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents.

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95% to 0.5% of at least one compound of the present invention in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, one third or one fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.01 to about 10 mg/kg, preferably 0.1 to 5 mg/kg, when administered parenterally and from about 1 to about 100 mg/kg, preferably 5 to 50 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Data relating to the coronary vessel dilation effect of compounds representative of those of the present invention is given below in Table I. The data was obtained by measuring the increase in oxygen saturation in the coronary sinus of narcotized, heart-catheterized mongrel dogs.

TABLE I

| Compound[1] | Dose[2] I.V. | Rise in $O_2$[3] Saturation | Return to[4] Normal $O_2$ Values |
|---|---|---|---|
| 1 | 0.05 | 24 | 20 |
| 2 | 0.5 | 34 | 30 |
| 2a | 0.1 | 32 | 20 |
| 3 | 0.5 | 46 | 60 |
| 4 | 0.5 | 26 | 30 |
| 6 | 0.5 | 32 | 60 |
| 8 | 0.5 | 27 | 45 |
| 15 | 0.01 | 28 | 30 |
| 16 | 0.05 | 33 | 60 |
| 17 | 0.02 | 26 | 30 |
| 24 | 0.5 | 24 | 30 |
| 25 | 0.3 | 20 | 30 |
| 27 | 0.1 | 20 | 60 |
| 29 | 0.5 | 26 | >20 |
| 30 | 0.02 | 27 | 60 |
| 31 | 0.5 | 26 | 60 |
| 32 | 0.2 | 29 | >120 |
| 33 | 0.5 | 24 | 45 |
| 37 | 0.5 | 23 | 20 |
| 43 | 0.3 | 24 | 30 |

Notes
[1]Compounds are identified by the number of the Preparative Example describing their production.
[2]Expressed as mg/kg body weight.
[3]Expressed as percentage rise in the oxygen saturation in the coronary sinus.
[4]I. e., Time for oxygen saturation in coronary sinus to return to its predosage value, expressed in minutes.

PREPARATIVE EXAMPLES

EXAMPLE 1

2,6-Dimethyl-4-(2'-nitrophenyl)-1.4-dihydropyridine-3,5-dicarboxylic acid di-(β-pyridyl)-methyl ester

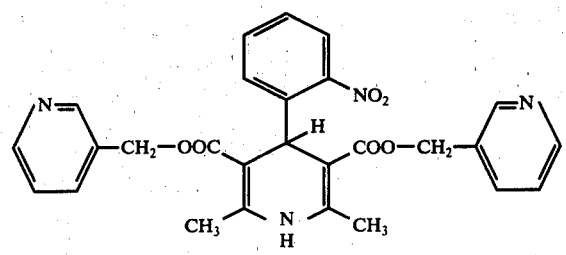

A solution of 7.5 g of 2-nitrobenzaldehyde, 20 g of acetoacetic acid methyl-β-pyridyl ester (boiling point at 0.5 mm Hg: 145°-150°) and 5 ccs. of ammonia in 30 ccs. of methanol is heated to the boil for 3 hours and evaporated, and after being taken up in acetone the product is precipitated as the HCl salt using hydrochloric acid. Yield 80%.

Crystals of melting point 170° – 172° C are obtained from isopropanol and a little methanol.

EXAMPLE 2

2,6-Dimethyl-4-(2'-nitrophenyl)-1,4-dihydropyridine-3,5- dicarboxylic acid di-(α-pyridyl)-methyl ester

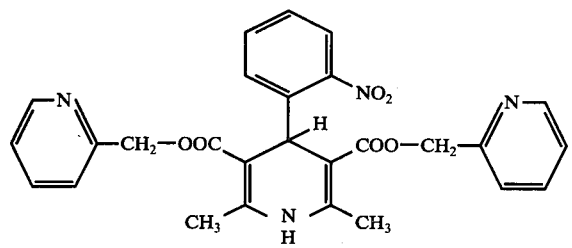

After heating a solution of 7.5 g of o-nitrobenzaldehyde, 20 g of acetoacetic acid methyl-α-pyridyl ester (boiling point at 0.5 mm Hg: 138°–140°) and 10 ccs. of ammonia in 30 ccs. of methanol for 3 hours, the mixture is concentrated and taken up in acetone, and the HCl salt is precipitated with hydrochloric acid in ether. Yield 90%.

After recrystallization from alcohol, canary-yellow crystals of melting point 206° – 208° C are obtained.

In the same manner:

a. 7.5 g of m-nitrobenzaldehyde, 20 g of acetoacetic acid methyl-α-pyridyl ester and 10 ccs. of ammonia in 30 ccs. of methanol yielded 2,6-dimethyl-4-(-b 3'-nitrophenyl)-1,4-dihydropyridine-3,5-dicarboxylic acid acid di-(α-pyridyl)-methyl ester as the hydrochloride, in yellow crystals of melting point 152° – 155° C, yield 88%, and b. 7.5 g of m-nitrobenzaldehyde, 20 g of acetoacetic acid methyl-β-pyridyl ester and 10 ccs. of ammonia in 30 ml of methanol yielded 2.6-dimethyl-4-(3'-nitrophenyl)-1,4-dihydropyridine-3,5-dicarboxylic acid di(β-pyridyl)-methyl ester as the hydrochloride in yellow crystals of melting point 202° – 204° C. Yield 85%.

EXAMPLE 3

2,6-4-(2'-trifluoromethylphenyl)-1,4-dihydropyridine-3,5-dicarboxylic acid di-(β-N-morpholino)-isopropyl ester

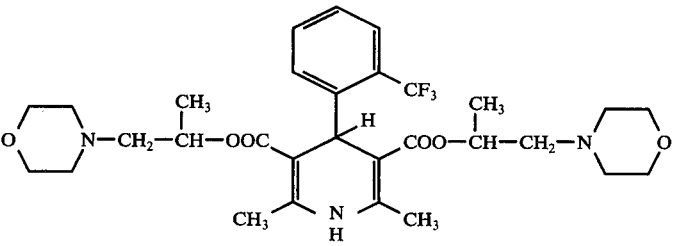

After heating a solution of 8.7 g of o-trifluoromethylbenzaldehyde, 23 g of acetoacetic acid β-moropholino-isopropyl ester (boiling point at 0.4 mm Hg: 126°) and 5 ccs. of ammonia for several hours, the misture is concentrated in vacuo and taken up in acetone-ether, and the hydrochloric acid salt is obtained with hydropchloricc acid in ether. Yield 70%.

Light yellow crystals of melting point 220°C as alcohol acetone.

EXAMPLE 4

2,6-Dimethyl-4-(3'-trifluoromethylphenyl)-1,4-dihydropyridine -3,5-dicarboxylic acid di-(β-pyridyl)-methyl ester

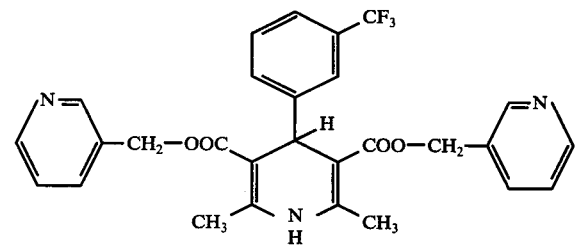

After heating 10 g of 3-trifluoromethyl-benzaldehyde and 25 g of acetoacetic acid methyl-β-pyridyl ester (boiling point 0.1 mm Hg: 125° C) and 6 ccs. of ammonia in 60 ccs. of alcohol for several hours, white crystals of melting point 198° C were obtained. Yield 55%.

EXAMPLE 5

2,6-Dimethyl-4-(4'-chlorophenyl)-1,4-dihydropyridine-3,5-dicarboxylic acid di-(β-N-morpholino)-ethyl ester.

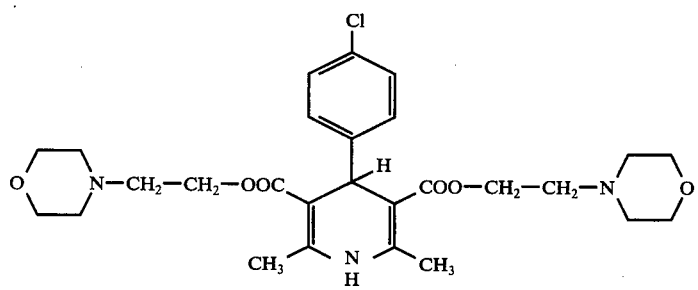

14 g of 4-chlorobenzaldehyde, 43 g of acetoacetic acid β-morpholinoethyl ester (boiling point at 0.5 mm Hg: 128° –130° C) and 10 ccs. of ammonia in 100 ccs. of methanol are heated to the boil for 5 hours and the mixture is filtered and concentrated in vacuo. It is taken up in ether and then precipitated as the hydrochloride with hydrochloric acid in ether. Crystals of melting point 178° - 180° C from alcohol. Yield 76%. a. In the same manner, 17 g of 2,4-dichlorobenzaldehyde, 43 g of acetoacetic acid β-morpholinoethyl ester and 10 ccs. of ammonia in 100 ccs. of methanol yield, 2,6-dimethyl-4-(2'-4'-dichlorophenyl)-1,4-dihydropyridine-3,5-dicarboxylic acid di-(β-N-morpholino)-ethyl ester as the hydrochloride, in yellow-green crystals of melting point 169° -171° C. Yield 66%.

EXAMPLE 6

2,6-Dimethyl-4-(3'-cyanophenyl)-1,4-dihydropyridine-3,5-dicarboxylic acid di-(β-N-morpholino)-isopropyl ester.

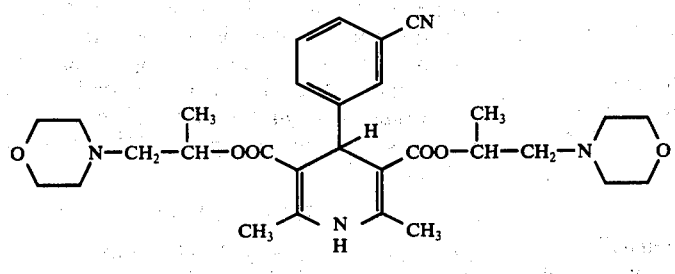

After boiling a solution of 6.5 g of 3-cyanobenzaldehyde, 23 g of acetoacetic acid 2-morpholino-isopropyl ester and 6 ccs. of ammonia for 8 hours, the mixture is evaporated in vacuo and taken up in acetone-ether, and the product is precipitated as the HCl salt with hydrochloris acid. Yellow crystals of melting point 156° C. Yield 90%.

EXAMPLE 7

2,6-Dimethyl-4-(4'-ethylsulphonylphenyl)-1.4-dihydropyridine-3,5-dicarboxylic acid di-(α-pyridyl)-methyl ester.

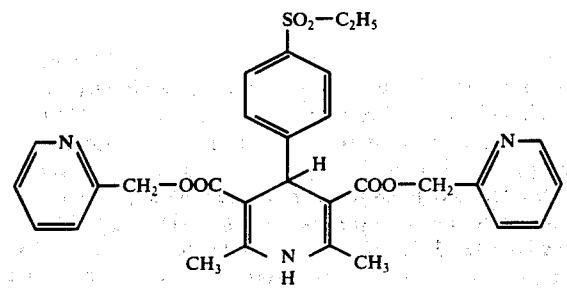

10 g of 4-ethylsulphonylbenzaldehyde, 5 ccs. of concentrated ammonia and 19.5 g. of acetoacetic acid (α-pyridyl)-methyl ester in 40 ccs. of alcohol are heated under reflux for 8 hours. The mixture is concentrated in vacuo and after addition of ether crystals which melt at 138° C. when recrystallized from alcohol are obtained. Yield 73%.

EXAMPLE 8

2,6-Dimethyl-4-(3'-azidophenyl)-1,4-dihydropyridine-3,5-dicarboxylic acid di-(β N-morpholino)-ethyl ester

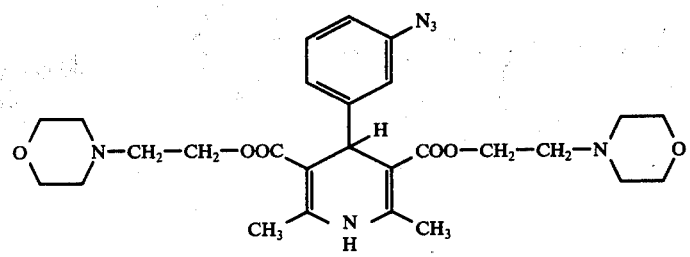

7.4 g of 3-azidobenzaldehyde, 23 g of acetoacetic acid 2-morpholinoethyl ester and 6 ccs. of ammonia in 30 ccs. of alcohol are heated to the boil overnight and after precipitation with hydrochloric acid in ether the HCl salt of melting point 183° C (alcohol/light beige) is obtained. Yield 69%.

EXAMPLE 9

2,6-Dimethyl-4-(4'-dimethylaminophenyl)-1,4-dihydropyridine-3,5-dicarboxylic acid di-(β-pyridyl)-methyl ester

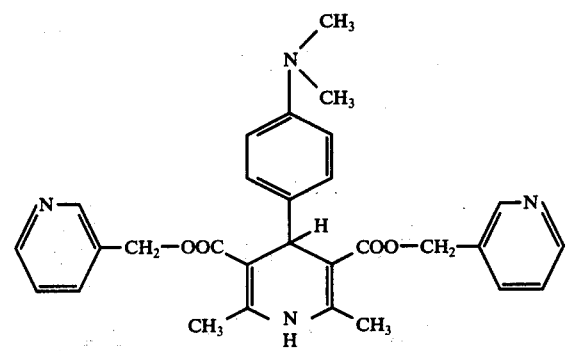

After heating 7.5 g of 4-dimethyl-aminobenzaldehyde, 20 g of acetoacetic acid methyl-β-pyridyl ester and 5 ccs. of ammonia in 30 ccs. of methanol for 3 hours, and concentrating the mixture, crystals of melting point 166° - 168° C. are obtained. Yield 43%.

EXAMPLE 10

2,6-Dimethyl-4-(α-pyridyl)-1,4-dihydropyridine-3,5-dicarboxylic acid di-(α-pyridyl)-methyl ester

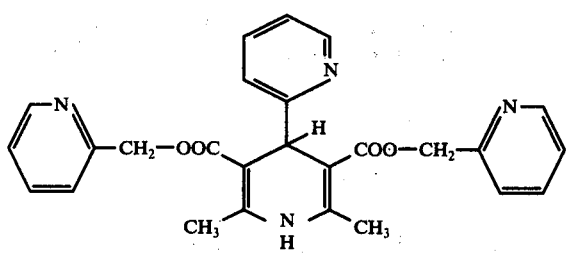

A solution of 5.3 g of pyridin-2-aldehyde, 20 g of acetoacetic acid methyl-α-pyridyl ester and 6 ccs. of ammonia in 100 ccs. of alcohol is heated to the boil for 7 hours and after evaporation crystals (yellowish) of melting point 146° – 148° C are obtained from alcohol. Yield 39%.

EXAMPLE 11

2,6-Dimethyl-4-(3'-nitro-6'-methylmercaptophenyl)-1,4-dihydro-3,5-dicarboxylic acid di-(β-pyridyl)-methyl ester

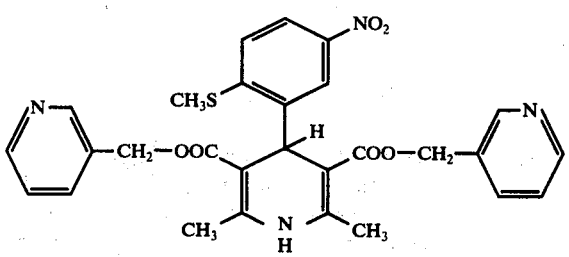

10 g of 3-nitro-6-methylmercaptobenzaldehyde (melting point 163° C), 20 g of acetoacetic acid methyl-β-pyridyl ester and 6 ccs. of ammonia in 80 ccs. of alcohol are heated to the boil for several hours, the mixture is filtered hot after addition of charcoal and is concentrated, and the residue is recrystallized from 200 ccs. of acetone.

Yellow crystals of melting point 182° – 184° C. Yield 52%.

EXAMPLE 12

2,6-Dimethyl-4-(4',6'-dimethoxy-5-pyrimidyl)-1,4-dihydro-pyridine-3,5-dicarboxylic acid di-(β-N-morpholino)-isopropyl ester

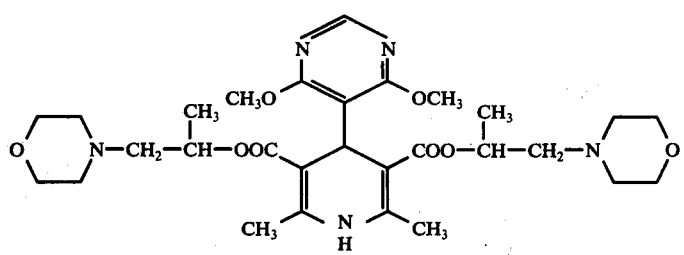

8.4 g of 4,6-dimethoxy-pyrimidin-5-aldehyde, 23 g of acetoacetic acid β-morpholinoisopropyl ester and 5 ccs. of ammonia in 30 ccs. of methanol are heated to the boil for several hours, the mixture is evaporated and taken up in acetone and the product is precipitated as the hydrochloride with hydrochloric acid in ether.

Beige crystals of melting point 216° – 218° C from alcohol. Yield 47%.

EXAMPLE 13

1,2,6-Trimethyl-4-phenyl-1,4-dihydropyridine-3,5-dicarboxylic acid di-(β-N-morpholino)-isopropyl ester

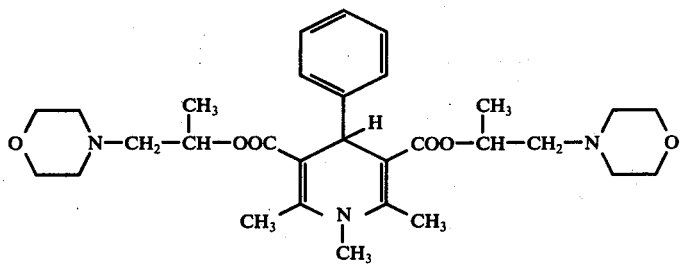

5 g of benzaldehyde, 23 g of acetoacetic acid 2-morpholino-isopropyl ester and 4 g of methylamine hydrochloride in 25 ccs. of pyridine are heated to about 90° C for 6 hours; the mixture is introduced into ice water and taken up in ether, and after washing with water and drying over sodium sulphate, hydrochloric acid in ether yields the HCl salt in yellow crystals of melting point 159° C. Yield 75%.

EXAMPLE 14

1,2,6-Trimethyl-4-(2'-nitrophenyl)-1,4-dihydropyridine-3,5-dicarboxylic acid di-(β-N-morpholino)-isopropyl ester

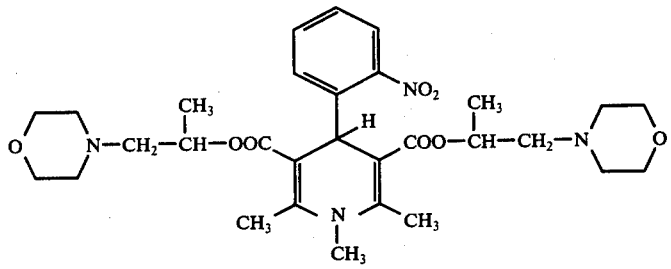

7.5 g of 2-nitrobenzaldehyde, 23 g of acetoacetic acid β-morpholino-isopropyl ester and 4 g of methylamine hydrochloride in 40 ccs. of pyridine are allowed to stand for 3 hours at 90° C; the mixture is introduced into ice water and taken up in ether, the ether solution is washed with water and dried over sodium sulphate and the product is precipitated as the hydrochloride with hydrochloric acid in ether. Yellow crystals of melting point 168° – 170° C. Yield 61%.

EXAMPLE 15

2,6-Dimethyl-4-(2'-nitrophenyl)-1,4-dihydropyridine-3,5-dicarboxylic acid 3-(α-pyridyl)-methyl ester 5-methyl ester

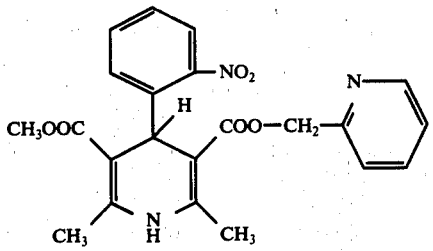

A solution of 7.5 g of o-nitrobenzaldehyde, 9.7 g of acetoacetic acid (α-pyridyl)-methyl ester, and 6 g of β-aminocrotonic acid methyl ester in 40 ccs. of alcohol is heated to the boil for several hours and the product is filtered off.

Yellow crystals (alcohol) of melting point 196° C. Yield 65%.

EXAMPLE 16

2,6-Dimethyl-4-(2'-nitrophenyl)-1,4-dihydropyridine-3,5-dicarboxylic acid 3-(α-pyridyl)-methyl ester 5-isopropyl ester

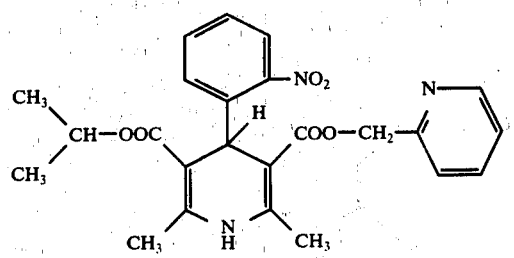

7.5 g of o-nitrobenzaldehyde, 9.7 g of acetoacetic acid (α-pyridyl)-methyl ester and 7.2 g of β-aminocrotonic acid isopropyl ester in 40 ccs. of alcohol are heated to the boil overnight and after cooling, filtration and rinsing with alcohol and ether ochre-yellow crystals of melting point 175° C are obtained. Yield 70%.

EXAMPLE 17

2,6-Dimethyl-4-(2'-nitrophenyl)-1,4-dihydropyridine-3,5-dicarboxylic acid 3-(α-pyridyl)-methyl ester 5-methoxyethyl ester

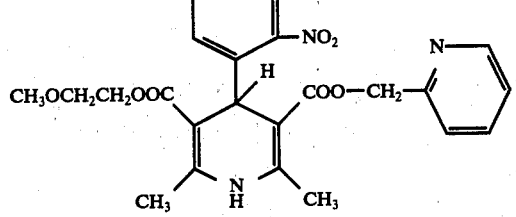

After heating a solution of 7.5 g of 2-nitrobenzaldehyde, 9.7 g of acetoacetic acid (α-pyridyl)-methyl ester and 8 g of β-aminocrotonic acid β-methoxyethyl ester in 40 ccs. of alcohol for several hours, yellow crystals of melting point 123° C are obtained. Yield 55%.

EXAMPLE 18

2,6-Dimethyl-4-(2'-trifluoromethyl-4'-nitrophenyl)-1,4-dihydropyridine-3,5-dicarboxylic acid 3-(α-pyridyl)-methyl ester 5-methyl ester

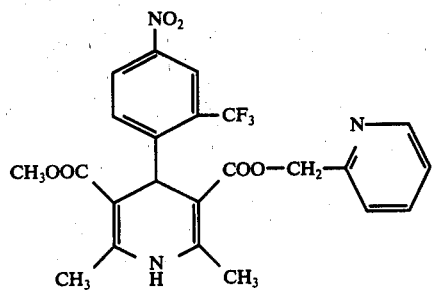

After heating a solution of 11 g of 2-trifluoromethyl-4-nitrobenzaldehyde, 9.7 g of acetoacetic acid methyl-pyridyl ester and 6 g of β-aminocrotonic acid methyl ester in 40 ccs. of alcohol for several hours, yellow crystals of melting point 155° C are obtained (on cooling). Yield 55%.

EXAMPLE 19

2,6-Dimethyl-4-(3'-fluoro-4'-methoxyphenyl)-1,4-dihydropyridine-3,5-dicarboxylic acid 3-(β-morpholino)-ethyl ester 5-methyl ester

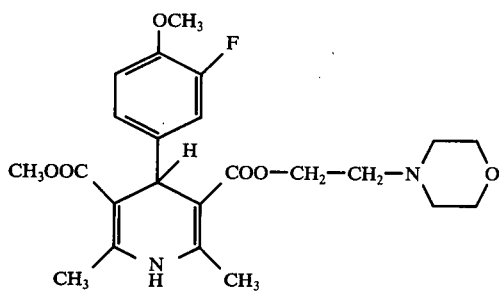

After heating a solution of 7.7 g of 3-fluoro-4-methoxybenzaldehyde, 11 g of acetoacetic acid β-morpholino-ethyl ester and 6 g of β-aminocrotonic acid methyl ester in 40 ccs. of alcohol for several hours, the mixture is evaporated in vacuo, the residue is taken up in ether and the product is precipitated as the hydrochloride with hydrochloric acid in ether.

The free compound is obtained from the yellow hydrochloric acid salt as white crystals of melting point 105° C (benzene/petroleum ether). Yield 75% (HCl salt).

EXAMPLE 20

2,6-Dimethyl-4-(4',6'-dimethoxy-5-pyrimidyl)-1,4-dihydro-pyridine-3,5-dicarboxylic acid 3-(α-pyridyl)-methyl ester 5-methyl ester

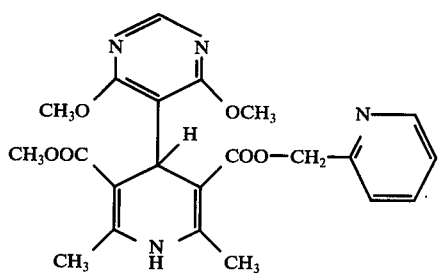

A solution of 5 g of 4,6-dimethoxypyrimidin-5-aldehyde, 5.9 g of acetoacetic acid α-pyridyl ester and 3.6 g of β-aminocrotonic acid methyl ester in 30 ccs. of alcohol is heated to the boil for 8 hours and the free compound is obtained, via the HCl salt (light yellow crystals) as white crystals of melting point 57° – 58° C. Yield 84%.

EXAMPLE 21

2,6-Dimethyl-4-(4'-acetaminophenyl)-1,4-dihydropyridine-3,5-dicarboxylic acid 3-(α-pyridyl)-methyl ester 3-methyl ester

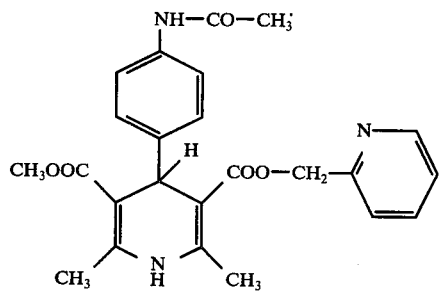

8.2 g of 4-acetaminobenzaldehyde, 9.7 g of acetoacetic acid (α-pyridyl)-methyl ester and 6 g of β-aminocrotonic acid methyl ester in 40 ccs. of alcohol are heated to the boil for 4 to 6 hours and concentrated, and, after addition of ether and cooling, yellow crystals of melting point 199° C are obtained. Yield 75%.

EXAMPLE 22

2,6-Dimethyl-4-(2'-nitrophenyl)-1,4-dihydropyridine-3,5-dicarboxylic acid 3-(γ-N-N'-methylpiperazino)-propyl ester 5-methyl ester

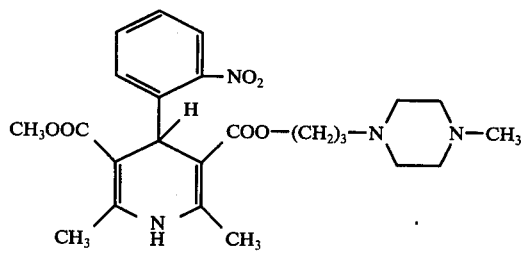

After heating a solution of 7.5 g of o-nitrobenzaldehyde, 12 g of acetoacetic acid (γ-N-N'-methylpiperazino)-n-propyl ester (boiling point 140° C at 1 mm Hg) and 6 g of β-aminocrotonic acid methyl ester in 40 ccs. of alcohol for several hours, the mixture is concentrated and taken up in ether and the product is precipitated as the hydrochloride with hydrochloric acid in ether and recrystallized from alcohol. Light yellow crystals of melting point 240° C. Yield 75%.

EXAMPLE 23

1,2,6-Trimethyl-4-(3'-nitrophenyl)-1,4-dihydropyridine-3,5-dicarboxylic acid 3-(β-diethylamine)-ethyl ester 5-methyl ester

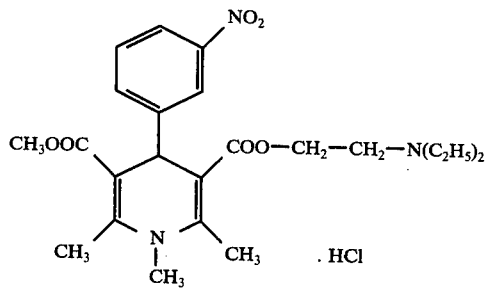

11 g of 1,2,6-trimethyl-4-(3'-nitrophenyl)-1,4-dihydropyridine-3-carboxylic acid-5-carboxylic acid methyl ester (melting point 166°) and 7 ccs. of diethyl-(2-chloro-ethyl)-amine in 200 ccs. of isopropyl alcohol are heated overnight; the mixture is filtered and the reaction product is obtained as the hydrochloride (precipitation with hydrochloric acid) in crystals of melting point 178° – 180° C (page beige). Yield 65%.

EXAMPLE 24

2,6-Dimethyl-4-phenyl-1,4-dihydropyridine-3,5-dicarboxylic acid 3-(β-N-morpholino)-ethyl ester 5-ethyl ester

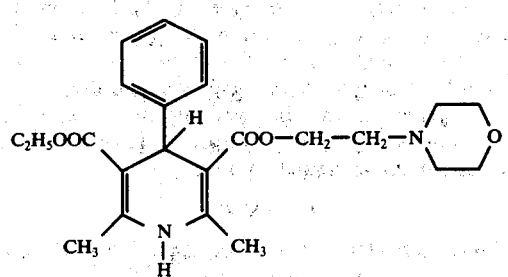

After heating a solution of 5 ccs. of benzaldehyde, 11 g of acetoacetic acid (β-N-morpholino)-ethyl ester and 6 g of β-aminocrotonic acid methyl ester in 40 ccs. of alcohol for several hours, the mixture is concentrated and after taking up in ether, the hydrochloride salt is precipitated with hydrochloric acid. Yellow crystals, yield 80%.

The free compound is obtained as white crystals of melting point 112° C (benzene-petroleum ether).

EXAMPLE 25

2,6-Dimethyl-4-phenyl-1,4-dihydropyridine-3,5-dicarboxylic acid 3-(α-pyridyl)-methyl ester 5-methyl ester

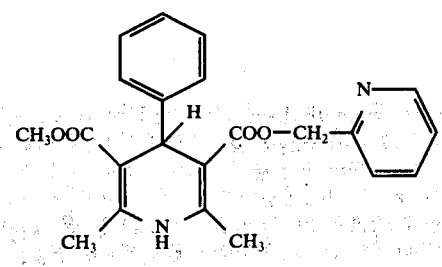

5 ccs. of benzaldehyde, 9.7 g of acetoacetic acid (α-pyridyl)-methyl ester and 6 g of β-aminocrotonic acid methyl ester in 40 ccs. of alcohol are heated to the boil for several hours, the mixture is concentrated and the product is precipitated as the HCl salt with hydrochloric acid. Light yellow crystals, yield 85%.

EXAMPLE 26

2,6-Dimethyl-4-phenyl-1,4-dihydropyridine-3,5-dicarboxylic acid 3-(γ-N-N'-methylpiperazino)-n-propyl ester 5-carboxylic acid methyl ester

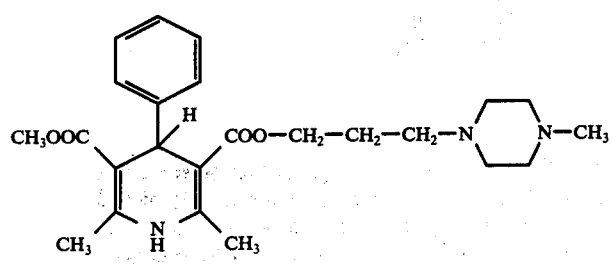

After heating a solution of 5 ccs. of benzaldehyde, 12 g of acetoacetic acid (γ-N-N'-methylpiperazino)-n-propyl ester and 6 g of β-aminocrotonic acid methyl ester in 40 ccs. of alcohol under reflux for several hours, yellow crystals are obtained as the HCl salt after working up as above described. Yield 90%.

EXAMPLE 27

2,6-Dimethyl-4-(2'-chlorophenyl)-1,4-dihydropyridine-3,5-dicarboxylic acid 3-(α-pyridyl)-methyl ester 5-methyl ester

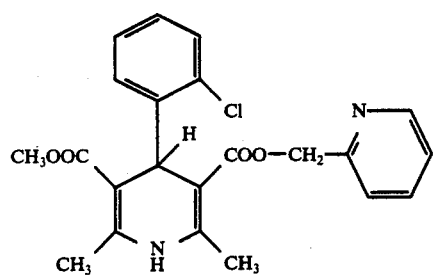

7 g of 2-chlorobenzaldehyde, 9.7 g of acetoacetic acid (α-pyridyl)-methyl ester and 6 g of β-aminocrotonic acid methyl ester in 40 ccs. of alcohol are heated to the boil for 4 to 6 hours and concentrated, the residue is taken up in ether and the HCl salt is precipitated with hydrochloric acid in ether. Yellow crystals, 85% yield.

EXAMPLE 28

2,6-Dimethyl-4-(2'-chlorophenyl)-1,4-dihydropyridine-3,5-dicarboxylic acid 3-(γ-N,N'-methylpiperazino)-methyl ester 5-methyl ester

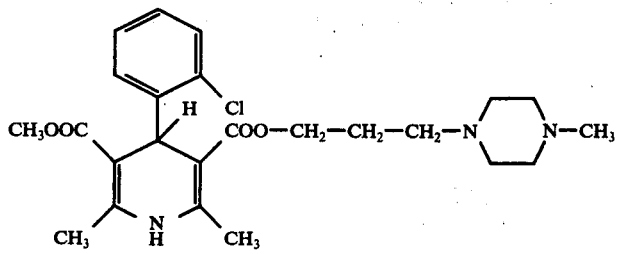

7 g of 2-chlorobenzaldehyde, 12 g of acetoacetic acid (γ-N,N'-methypiperazino)-methyl ester and 6 g of β-aminocrotonic acid methyl ester in 60 ccs. of alcohol are heated to the boil overnight and finally concentrated, the residue is taken up in ether and the product is precipitated as the hydrochloride salt with hydrochloric acid. Yellow crystals, yield 75%.

EXAMPLE 29

2,6-Dimethyl-4-(2'-azidophenyl)-1,4-dihydropyridine-3,5-dicarboxylic acid 3-(α-pyridyl)-methyl ester 5-methyl ester

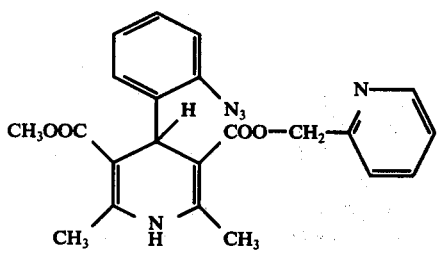

A solution of 7.4 g of 2-azidobenzaldehyde, 9.7 g of acetoacetic acid (α-pyridyl)-methyl ester and 6 g of β-aminocrotonic acid methyl ester in 40 ccs. of alcohol is heated to the boil for approximately 6 hours, concentrated and treated with ether and subsequently with hydrochloric acid in ether. The hydrochloride salt is precipitated as ochre yellow crystals, yield 75%.

EXAMPLE 30

2,6-Dimethyl-4-(2'-trifluoromethylphenyl)-1,4-dihydropyridine-3,5-dicarboxylic acid 3-(α-pyridyl)-methyl ester 5-methyl ester

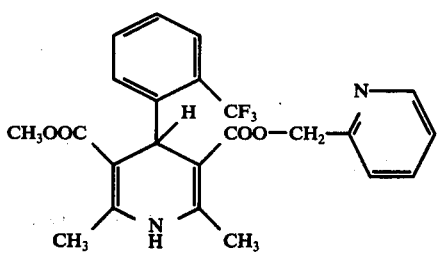

After heating a solution of 8.7 g of 2-trifluoromethylbenzaldehyde, 6 g of acid methyl ester and 9.7 g of acetoacetic acid (α-pyridyl)-methyl ester in 40 ccs. of alcohol for several hours and concentrating, the mixture is taken up in ether and the reaction product is precipitated as the hydrochloride salt with hydrochloric acid. Yellow crystals, yield 75%.

EXAMPLE 31

2,6-Dimethyl-4-(2'-trifluoromethylphenyl)-1,4-dihydropyridine-3,5-dicarboxylic acid 3-(γ-N,N'-methylpiperazino)-n-propyl ester 5-methyl ester

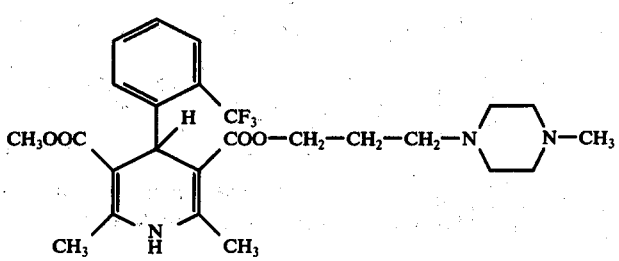

8.7 g of 2-trifluoromethylbenzaldehyde, 12 g of acetoacetic acid (γ-N,N'-methylpiperazino)-n-propyl ester and 6 g of β-aminocrotonic acid methyl ester in 40 ccs. of alcohol are heated to the boil overnight and after concentration the product is precipitated as the HCl salt with hydrochloric acid. Yellow crystals, yield 75%.

EXAMPLE 32

2,6-Dimethyl-4-(3'-nitrophenyl)-1,4-dihydropyridine-3,5-dicarboxylic acid 3-(β-N-morpholino)-ethyl ester 5-methyl ester

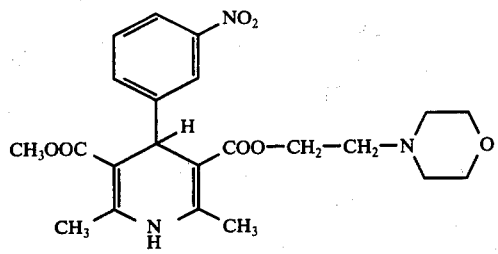

A solution of 7.5 g of 3-nitrobenzaldehyde, 11 g of acetoacetic acid (β-N-morpholino)-ethyl ester and 6 g of β-aminocrotonic acid methyl ester in 40 ccs. of alcohol is heated to the boil overnight and concentrated, and the HCl salt is precipitated with hydrochloric acid. Light yellow crystals, yield 90%.

EXAMPLE 33

2,6-Dimethyl-4-(3'-nitrophenyl)-1,4-dihydropyridine-3,5-dicarboxylic acid 3-(γ-N,N'-methylpiperazino)-n-propyl ester 5-methyl ester

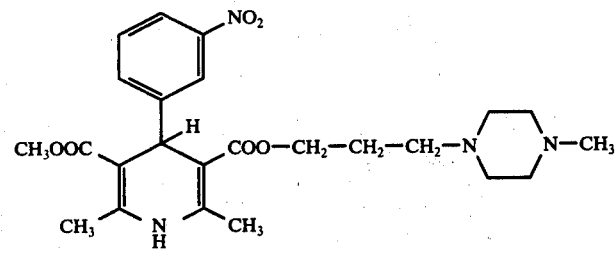

After heating a solution of 7.5 g of 3-nitrobenzaldehyde, 12 g of acetoacetic acid (γ-N,N'-methylpiperazino)-n-propyl ester and 6 g of β-aminocrotonic acid methyl ester in 40 ccs. of alcohol for 6 hours, the mixture is concentrated and taken up in ether and the product is precipitated as the HCl salt with hydrochloric acid. Ochre-yellow crystals, yield 65%.

EXAMPLE 34

2,6-Dimethyl-4-(4'-mercaptophenyl)-1,4-dihydropyridine-3,5-dicarboxylic acid 3-(β-N-morpholino)-ethyl ester 5-methyl ester

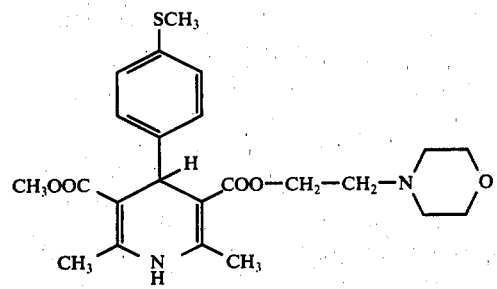

After heating a solution of 7.6 g of 4-mercaptobenzaldehyde, 10.8 g of acetoacetic acid (β-N-morpholino)-ethyl ester and 6 g of β-aminocrotonic acid methyl ester in 40 ccs. of alcohol for several hours, the mixture is concentrated and taken up in ether and the HCl salt is precipitated with hydrochloric acid in ether. Light yellow crystals, yield 85%.

EXAMPLE 35

2,6-Dimethyl-4-(α-pyridyl)-1,4-dihydropyridine-3,5-dicarboxylic acid 3-(β-N-morpholino)-isopropyl ester 5-methyl ester

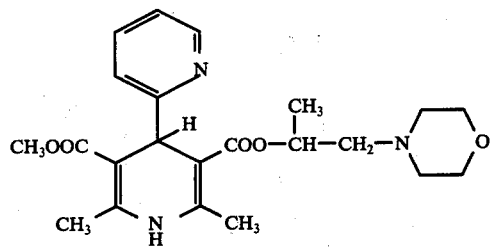

After heating a solution of 10.5 ccs. of α-pyridinaldehyde, 23 g of acetoacetic acid (β-N-morpholino)-isopropyl ester and 13 g of β-aminocrotonic acid methyl ester in 80 ccs. of alcohol to the boil for several hours, the mixture is concentrated and taken up in ether and the product is precipitated as the hydrochloride with hydrochloric acid in ether. Ochre-yellow crystals, yield 90%.

EXAMPLE 36

2,6-Dimethyl-4-(2'-bromo-5'-furyl)-1,4-dihydropyridine-3,5-dicarboxylic acid 3-(α-pyridyl)-methyl ester 5-methyl ester

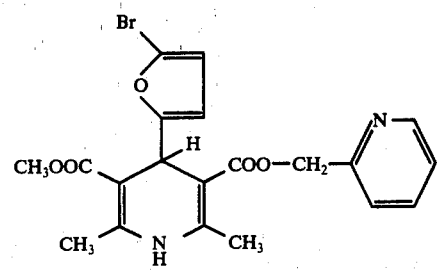

8.8 g of 5-bromo-furfurol, 9.7 g of acetoacetic acid (α-pyridyl)-methyl ester and 6 g of β-aminocrotonic acid methyl ester in 40 ccs. of alcohol are heated to the boil overnight. After working up and precipitation, the HCl salt is obtained with hydrochloric acid as light yellow crystals. Yield 70%.

EXAMPLE 37

2,6-Dimethyl-4-(2'-nitro-5-thenyl)-1,4-dihydropyridine-3,5-dicarboxylic acid 3-(α-pyridyl)-methyl ester 5-methyl ester

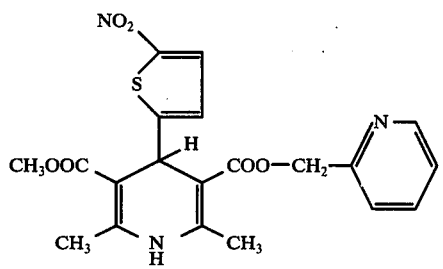

7.9 g of 5-nitrobenzaldehyde, 9.7 g of acetoacetic acid (α-pyridyl)-methyl ester and 6 g of β-aminocrotonic acid methyl ester in 40 ccs. of alcohol are heated to the boil for 10 hours. The HCl salt is obtained with hydrochloric acid in ochre-yellow crystals, yield 75%.

EXAMPLE 38

1,2,6-Trimethyl-4-(3'-nitrophenyl)-1,4-dihydropyridine-3,5-dicarboxylic acid 3-(α-pyridyl)-methyl ester 5-methyl ester

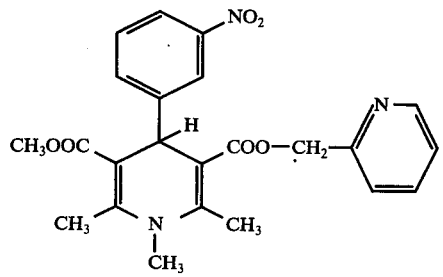

13 g of 3'-nitrophenylbenzylideneacetoacetic acid methyl ester (melting point 105° C), 9.7 g of acetoacetic acid (α-pyridyl-methyl ester and 4g of methylamine hydrochloride in 40 ccs. of pyridine are heated to about 90° C for 2 to 3 hours, the mixture is introduced into water and extracted with ether, and after washing and drying the product is precipitated as the hydrochloride with hydrochloric acid in ether. Ochre-yellow crystals, yield 76%

EXAMPLE 39

1,2,6-Trimethyl-4-(3'-nitrophenyl)-1,4-dihydropyridine-3,5-dicarboxylic acid 3-(γ-N,N'-methylpiperazino)-n-propyl ester 5-methyl ester

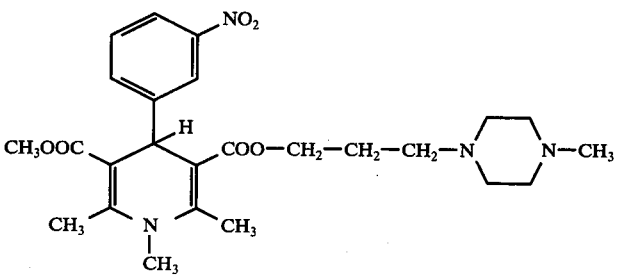

12.5 g of 3-nitrophenylbenzylideneacetoacetic acid methyl ester, 12 g of acetoacetic acid ('-methylpiperazino)-n-propyl ester and 4 g of methylamine hydrochloride in 40 ccs. of pyridine, are heated to about 90° C for 5 hours. Thereafter the mixture is introduced into water/ice and decanted, the residue is taken up in ether, and after washing and drying the solvent is distilled off. Yellow crystals of melting point 131° C from ether/petroleum ether. Yield 27%.

EXAMPLE 40

2,6-Dimethyl-4-(4'-nitrophenyl)-1,4-dihydropyridine-3,5-dicarboxylic acid 3-(β-N-morpholino)-ethyl ester 5-methyl

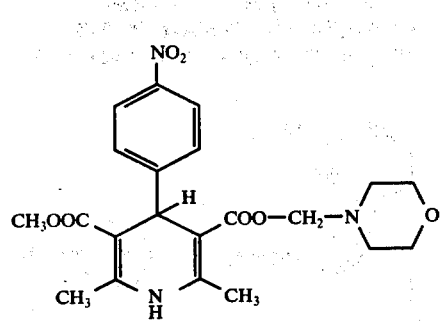

After heating a solution of 15 g of 4-nitrobenzaldehyde, 11 g of acetoacetic acid (β-N-morpholino)-ethyl ester and 6 g of aminocrotonic acid methyl ester in 40 ccs. of alcohol under reflux for several hours, light yellow crystals are obtained as the HCl salt with hydrochloric acid. Yield 75%.

EXAMPLE 41

2,6-Dimethyl-4-styryl-1,4-dihydropyridine-3,5-dicarboxylic acid 3-(γ-N,N'-methylpiperazino)-propyl ester 5-methyl ester

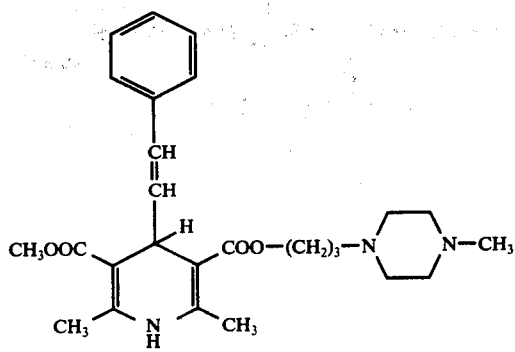

6.6 g of cinnamaldehyde, 6 g of β-aminocrotonic acid methyl ester and 12 g of acetoacetic acid (γ-N,Nester in 40 ccs. of ethanol are heated to the boil overnight and after concentration the hydrochloric acid salt is precipitated from the solution of hydrochloric acid in ether. Orange crystals, yield 70%.

EXAMPLE 42

2,6-Dimethyl-4-(S-phenyl-ethyl)-1.4-dihydropyridine-3.5-dicarboxylic acid 3-(γ-N,N'-methylpiperazino)-propyl ester 5-methyl ester

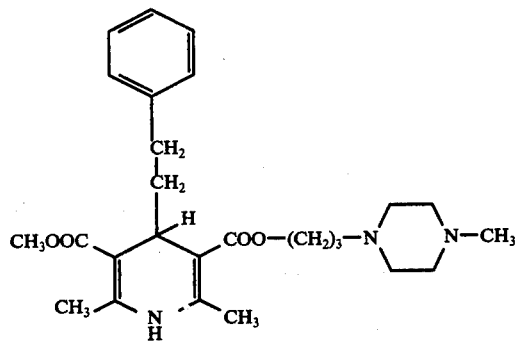

A solution of 6.7 g of hydrocinnamaldehyde, 12 g of acetoacetic acid (γ-N,N'-methylpiperazino)-propyl ester and 6 g of β-aminocrotonic acid methyl ester in 40 ccs. of ethanol is heated to the boil for 5 to 6 hours and after concentration the reaction product is precipitated as the hydrochloric acid salt with hydrochloric acid. Yellow crystals, yield 55%.

EXAMPLE 43

2,6-Dimethyl-4-(3'-methoxyphenyl)-1,4-dihydropyridine-3,5-dicarboxylic acid 3-(γ-N,N'-methylpiperazino)-propyl ester 5-methyl ester

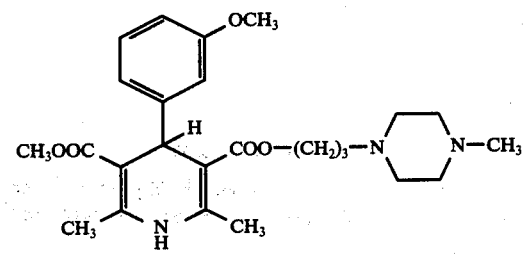

A solution of 6.8 g of 3-methoxybenzaldehyde, 5.8 g of β-aminocrotonic acid methyl ester and 12 g of acetoacetic acid (γ-N,N'-methylpiperazino)-propyl ester in 40 ccs. of ethanol is heated to the boil overnight and evaporated and after addition of ether the reaction product is precipitated as the hydrochloric acid salt. Light yellow crystals, yield 45%.

EXAMPLE 44

2,6-Dimethyl-4-(4'-quinolyl)-1,4-dihydropyridine-3,5-dicarboxylic acid 3-(γ-N,N'-methylpiperazino)-propyl ester 5-methyl ester.

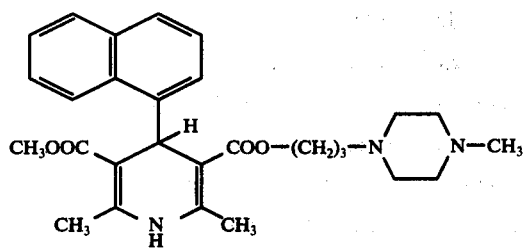

After heating a solution of 7.9 g of quinolin-4-aldehyde, 12 g of acetoacetic acid (γ-N,N'-methylpiperazino)-propyl ester and 5.8 of β-aminocrotonic acid methyl ester in 40 ccs. of ethanol under reflux for 8 hours the mixture is evaporated and taken up in ether and the product is precipitated as the hydrochloride with hydrochloric acid in ether. Yellow crystals, yield 65%.

EXAMPLE 45

2,6-Dimethyl-4-(α-naphthyl)-1,4-dihydropyridine-3,5-dicarboxylic acid 3-(γ-N,N'-methylpiperazino)-propyl ester

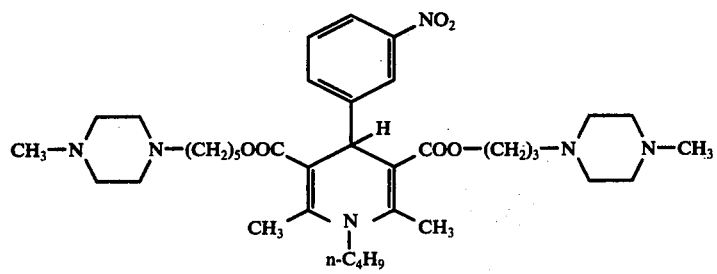

8 g of α-naphthaldehyde, 12 g of acetoacetic acid (γ-N,N'-methylpiperazino)-propyl ester and 5.8 g of γ-aminocrotonic acid methyl ester in 40 ccs. of alcohol are heated to the boil for several hours and evaporated, the residue is taken up in ether and the reaction product is precipitated as the hydrochloride salt with hydrochloric acid. Light yellow crystals, yield 60%.

EXAMPLE 46

1-Isopropyl-2,6-dimethyl-4-(3'-nitrophenyl)-1,4-dihydropyridine-3,5-dicarboxylic acid di(γ-N,N'-methylpiperazino)-propyl ester

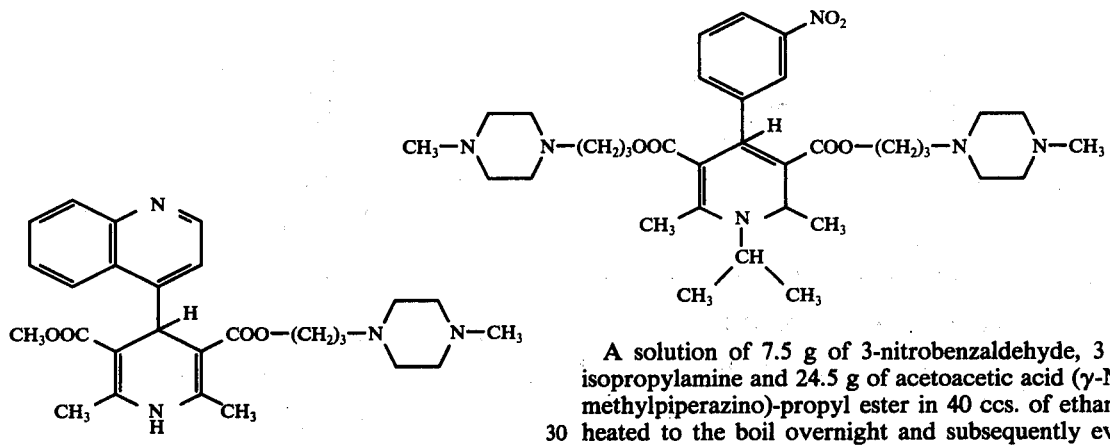

A solution of 7.5 g of 3-nitrobenzaldehyde, 3 g of isopropylamine and 24.5 g of acetoacetic acid (γ-N,N'-methylpiperazino)-propyl ester in 40 ccs. of ethanol is heated to the boil overnight and subsequently evaporated, and after addition of ether the product is precipitated as the hydrochloride salt with hydrochloric acid. Yellow crystals, yield 60%.

EXAMPLE 47

1-n-Butyl-2,6-dimethyl-4-(3'-nitrophenyl)-1,4-dihydropyridine-3,5-dicarboxylic acid di(γ-N,N'-methylpiperazino)-propyl ester A solution of 7.5 g of 3-nitrobenzaldehyde, 4 g of n-butylamine and 24.2 g of acetoacetic acid (γ-N,N'-methylpiperazino)-propyl ester in 40 ccs. of ethanol is heated overnight under a reflux condenser and evaporated, and the hydrochloride salt is precipitated from the solution of hydrochloric acid in ether. Yellow crystals, yield 65%.

EXAMPLE 48

1,2,6-Trimethyl-4-(3'-nitrophenyl)-1,4-dihydropyridine-3,5-dicarboxylic acid 3-(γ-dimethylamino)-propyl ester 5-ethyl ester

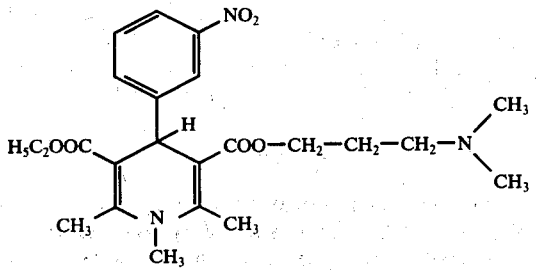

18 g of 1,2,6-trimethyl-4-(3'-nitrophenyl)-1,4-dihydropyridine-3-carboxylic acid-5-carboxylic acid ethyl ester (melting point 167° C) in 180 ccs. of ethanol are heated to the boil, a solution of 1.15 g of sodium in 50 ccs. of ethanol is next added, followed by 7.5 g of γ-dimethylamino-propyl chloride (dropping funnel), and the mixture is kept at the boil for several hours. After evaporation, the residue is taken up in ether, the ether is evaporated and the yellow reaction product (yield 95%) is recrystallized from ligroin. White crystals of melting point 103° C are obtained.

What is claimed is:

1. A pharmaceutical composition useful for effecting coronary vessel dilation in humans and animals and for treating hypertension in humans and animals which comprises a coronary vessel dilating amount or an antihypertensive amount of a compound of the formula:

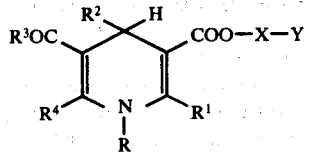

or a pharmaceutically acceptable nontoxic salt thereof wherein

R is hydrogen, straight- or branched-chain lower alkyl, lower alkenyl or lower alkynyl;

$R^1$ and $R^4$ are the same or different and are each hydrogen or straight- or branched-chain lower alkyl;

X is straight- or branched-chain lower alkylene;

Y is the moiety NR'R" wherein R' and R" are the same or different and are each hydrogen or lower alkyl $R^2$ is phenyl unsubstituted or substituted by 1, 2 or 3 substituents selected from the group consisting of nitro, cyano, lower alkyl, lower alkoxy, phenyl, trifluoromethyl and halogen; benzyl; phenyl-ethyl; styryl; or naphthyl; and $R^3$ is alkoxyalkyl of up to 6 carbon atoms in both moieties; lower alkyl; or lower alkoxy;

in combination with a pharmaceutically acceptable diluent or carrier.

2. A composition according to claim 1 wherein

R is hydrogen, straight- or branched-chain alkyl of 1 to 4 carbon atoms or straight- or branched-chain alkenyl of 2 to 4 carbon atoms;

$R^1$ and $R^4$ are the same or different and are each hydrogen or straight- or branched-chain alkyl of 1 to 4 carbon atoms;

X is straight- or branched-chain alkylene of 1 to 4 carbon atoms;

R' and R" are the same or different and are each hydrogen or alkyl of 1 to 4 carbon atoms; and $R^2$ is phenyl unsubstituted or substituted by 1 or 2 nitro, cyano, alkyl of 1 to 4 carbon atoms, chloro, bromo or trifluoromethyl groups, or by 1 to 3 alkoxy groups of 1 to 4 carbon atoms; benzyl; phenylethyl; styryl; or naphthyl.

3. A composition according to claim 1 wherein the alkyl moiety of R has 1 to 3 carbon atoms and the alkyl moiety of $R^1$ and $R^4$ has 1 or 2 carbon atoms.

4. A composition according to claim 3 wherein $R^2$ is phenyl unsubstituted or substituted by nitro, cyano, chloro, bromo or trifluoromethyl.

5. A composition according to claim 1 wherein

R is hydrogen or straight- or branched-chain alkyl of 1 to 4 carbon atoms, $R^1$ and $R^4$ are the same or different and are each straight or branched-chain alkyl of 1 to 4 carbon atoms, X is straight- or branched-chain alkylene of 1 to 4 carbon atoms, Y is dimethylamino or diethylamino; and $R^2$ is phenyl; phenyl substituted by 1 or 2 substituents selected from the group consisting of nitro, cyano, chloro and trifluoromethyl 6. A composition according to claim 1 wherein R is hydrogen or straight- or branched-chain alkyl of 1 to 4 carbon atoms, $R^1$ is straight- or branched-chain alkyl of 1 to 3 carbon atoms, $R^4$ is straight- or branched-chain alkyl of 1 to 4 carbon atoms, X is straight- or branched-chain alkylene of 1 to 3 carbon atoms, Y is dimethylamino or diethylamino, $R^2$ is phenyl; phenyl substituted by nitro, nitro and trifluoromethyl, nitro and chloro, dinitro, trifluoromethyl, di-trifluoromethyl, chloro, dichloro, cyano or fluoro; and $R^3$ is straight- or branched-chain alkoxy of 1 to 4 carbon atoms.

7. A composition according to claim 1 wherein

R is hydrogen or lower alkyl; and $R^2$ is phenyl unsubstituted by nitro, cyano, trifluoromethyl or halogen.

8. A composition according to claim 1 wherein

R is hydrogen;

$R^1$ and $R^4$ are each lower alkyl;

R' and R" are different and are selected from the group consisting of hydrogen and lower alkyl;

$R^2$ is phenyl unsubstituted or substituted or substituted by nitro, cyano, trifluoromethyl or halogen; and $R^3$ is alkoxyalkyl of up to 6 carbon atoms in both moieties.

9. The composition according to claim 1 wherein the compound is 1,2,6-trimethyl-4-(3'-nitrophenyl)-1,4-dihydropyridine-3,5-dicarboxylic acid 3-(β-diethylamine)-ethyl ester 5-methyl ester.

10. The composition according to claim 1 wherein the compound is 1,2,6-trimethyl-4-(3'-nitrophenyl)-1,4-dihydropyridine-3,5-dicarboxylic acid 3-(γ-dimethylamino)-propyl ester 5-ethyl ester.

11. The composition according to claim 1 wherein the compound is 2,6-dimethyl-4-(2'-nitrophenyl)-1,4-dihydropyridine-3,5-dicarboxylic acid 3-(ester 5-methyl ester.

12. A method of effecting coronary vessel dilation in humans and animals and of treating hypertension in humans and animals which comprises administering to such human or animal a coronary vessel dilating amount or an antihypertensive amount of a compound of the formula

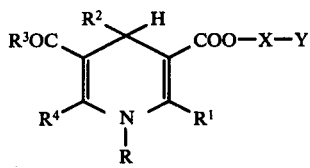

or a pharmaceutically acceptable nontoxic salt thereof wherein
R is hydrogen, straight- or branched-chain lower alkyl, lower alkenyl or lower alkynyl;
$R^1$ and $R^4$ are the same or different and are each hydrogen or straight- or branched-chain lower alkyl;
X is straight- or branched-chain lower alkylene;
Y is the moiety NR'R" wherein R' and R" are the same or different and are each hydrogen or lower alkyl;
$R^2$ is phenyl unsubstituted or substituted by 1, 2 or 3 substituents selected from the group consisting of nitro, cyano, lower alkyl, lower alkoxy, phenyl, trifluoromethyl and halogen; benzyl; phenyl-ethyl; styryl; and
$R^3$ is alkoxyalkyl of up to 6 carbon atoms in both moieties; lower alkyl; or lower alkoxy;
in combination with a pharmaceutically acceptable nontoxic diluent or carrier.

13. A method according to claim 12 wherein
R is hydrogen, straight- or branched-chain alkyl of 1 to 4 carbon atoms or straight- or branched-chain alkenyl of 2 to 4 carbon atoms;
$R^1$ and $R^4$ are the same or different and are each hydrogen or straight- or branched-chain alkyl of 1 to 4 carbon atoms;
X is straight- or branched-chain alkylene of 1 to 4 carbon atoms;
R' and R" are the same or different and are each hydrogen or alkyl of 1 to 4 carbon atoms; and
$R^2$ is phenyl unsubstituted or substituted by 1 or 2 nitro, cyano, alkyl of 1 to 4 carbon atoms, chloro, bromo or trifluoromethyl groups, or by 1 to 3 alkoxy groups of 1 to 4 carbon atoms; benzyl; phenyl-ethyl; styryl; or naphthyl.

14. A method according to claim 12 wherein the alkyl moiety of R has 1 to 3 carbon atoms and the alkyl moiety of $R^1$ and $R^4$ has 1 or 2 carbon atoms.

15. A method according to claim 12 wherein
$R^2$ is phenyl unsubstituted or substituted by nitro, cyano, chloro, bromo or trifluoromethyl.

16. A method according to claim 12 wherein
R is hydrogen or straight- or branched-chain alkyl of 1 to 4 carbon atoms,
$R^1$ and $R^4$ are the same or different and are each straight or branched-chain alkyl of 1 to 4 carbon atoms,
X is straight- or branched-chain alkylene of 1 to 4 carbon atoms,
Y is dimethylamino or diethylamino; and
$R^2$ is phenyl, phenyl substituted by 1 or 2 substituents selected from the group consisting of nitro, cyano, chloro and trifluoromethyl.

17. A method according to claim 12 wherein
R is hydrogen or straight- or branched-chain alkyl of 1 to 4 carbon atoms,
$R^1$ is straight- or branched-chain alkyl of 1 to 3 carbon atoms,
$R^4$ is straight- or branched-chain alkyl of 1 to 4 carbon atoms,
X is straight- or branched-chain alkylene of 1 to 3 carbon atoms,
Y is dimethylamino or diethylamino,
$R^2$ is phenyl; phenyl substituted by nitro, nitro and trifluoromethyl, nitro and chloro, dinitro, trifluoromethyl, chloro, dichloro, cyano or fluoro; and
$R^3$ is straight- or branched-chain alkoxy of 1 to 4 carbon atoms or methoxyethoxy.

18. A method according to claim 12 wherein
R is hydrogen or lower alkyl; and
$R^2$ is phenyl unsubstituted or substituted by nitro, cyano, trifluoromethyl or halogen.

19. A method according to claim 12 wherein
R is hydrogen;
$R^1$ and $R^4$ are each lower alkyl;
R' and R" are different and are selected from the group consisting of hydrogen and lower alkyl;
$R^2$ is phenyl unsubstituted or substituted by nitro, cyano, trifluoromethyl or halogen; and
$R^3$ is alkoxyalkyl of up to 6 carbon atoms in both moieties.

20. A method according to claim 12 wherein the compound is 1,2,6,-trimethyl-4-(3'-nitrophenyl)-1,4-dihydropyridine-3,5-dicarboxylic acid 3 β-diethylamine)-ethyl ester 5-methyl ester.

21. A method according to claim 12 wherein the compound is 1,2,6-trimethyl-4-(3'-nitrophenyl)-1,4-dihydropyridine-3,5-dicarboxylic acid 3(γ-dimethylamino)-propyl ester 5-ethyl ester.

22. A method according to claim 12 wherein the compound is 2,6-dimethyl-4-(2'-nitrophenyl)-1,4-dihydropyridine-3,5-dicarboxylic acid 3-(γ-dimethylamino)-propyl ester 5-methyl ester.

* * * * *